US008003782B1

(12) United States Patent
Brown et al.

(10) Patent No.: US 8,003,782 B1
(45) Date of Patent: Aug. 23, 2011

(54) PHARMACEUTICAL COMPOSITION OF COMPLEX CARBOHYDRATES AND ESSENTIAL OILS AND METHODS OF USING THE SAME

(75) Inventors: Harold G. Brown, Parkville, MO (US); Carol A. Cooper, Pittsburgh, PA (US); Kristina J. Hennessy, Parkville, MO (US); Karen K. Brown, Parkville, MO (US)

(73) Assignee: Dermal Research Laboratories, Inc., Parkville, MO (US)

( * ) Notice: Subject to any disclaimer, the term of this patent is extended or adjusted under 35 U.S.C. 154(b) by 0 days.

(21) Appl. No.: 09/890,425

(22) PCT Filed: Feb. 1, 2000

(86) PCT No.: PCT/US00/02328
§ 371 (c)(1),
(2), (4) Date: Feb. 19, 2002

(87) PCT Pub. No.: WO00/44367
PCT Pub. Date: Aug. 3, 2000

Related U.S. Application Data

(60) Provisional application No. 60/117,988, filed on Feb. 1, 1999, provisional application No. 60/127,749, filed on Apr. 5, 1999, provisional application No. 60/137,098, filed on Jun. 2, 1999, provisional application No. 60/142,306, filed on Jul. 3, 1999, provisional application No. 60/166,326, filed on Nov. 19, 1999.

(51) Int. Cl.
*C07H 5/04* (2006.01)
*C07H 5/06* (2006.01)
(52) U.S. Cl. ..................................... 536/55.2; 536/55.1
(58) Field of Classification Search ................... 514/54, 514/777; 424/439, 440; 536/123, 123.1, 536/55.1, 55.2
See application file for complete search history.

(56) References Cited

U.S. PATENT DOCUMENTS

| | | | |
|---|---|---|---|
| 3,895,107 A | 7/1975 | Morrison | |
| 4,141,973 A * | 2/1979 | Balazs | 514/54 |
| 4,148,893 A | 4/1979 | Smith | |
| 4,248,861 A | 2/1981 | Schutt | |
| 4,303,676 A * | 12/1981 | Balazs | 514/773 |
| 4,440,777 A | 4/1984 | Zupan | |
| 4,463,016 A | 7/1984 | Burgess | |
| 4,474,763 A | 10/1984 | Lubowe | |
| 4,585,656 A | 4/1986 | Rosenthal et al. | |
| 4,707,354 A | 11/1987 | Garlen et al. | |
| 4,736,024 A * | 4/1988 | Della Valle et al. | 536/55.3 |
| 4,782,046 A | 11/1988 | Brown et al. | |
| 4,808,576 A | 2/1989 | Schultz et al. | |
| 4,895,727 A | 1/1990 | Allen | |
| 4,917,890 A | 4/1990 | McAnalley | |
| 4,933,183 A * | 6/1990 | Sharma et al. | 424/439 |
| 4,933,184 A | 6/1990 | Tsuk | |
| 4,973,473 A | 11/1990 | Schneider et al. | |
| 5,009,890 A | 4/1991 | Dipippo | |
| 5,013,726 A | 5/1991 | Ivy et al. | |
| 5,028,429 A | 7/1991 | Gochenouer | |
| 5,073,366 A | 12/1991 | Beck | |
| 5,079,260 A * | 1/1992 | Weitzberg et al. | 514/532 |
| 5,082,656 A | 1/1992 | Hui et al. | |
| 5,096,709 A | 3/1992 | Vandersloot | |
| 5,106,622 A | 4/1992 | Sherwood et al. | |
| 5,166,331 A | 11/1992 | della Valle et al. | |
| 5,179,086 A | 1/1993 | Flender | |
| 5,223,257 A | 6/1993 | Arora | |
| 5,266,318 A | 11/1993 | Taylor-McCord | |
| 5,331,012 A | 7/1994 | Riddick et al. | |
| 5,350,774 A | 9/1994 | Palou | |
| 5,559,103 A * | 9/1996 | Gaeta et al. | 514/54 |
| 5,604,200 A * | 2/1997 | Taylor-McCord | 514/8 |
| 5,773,425 A | 6/1998 | McAnalley et al. | |
| 5,888,984 A | 3/1999 | Brown | |
| 5,929,050 A | 7/1999 | Petito | |
| 5,965,152 A | 10/1999 | Galin et al. | |
| 6,083,933 A | 7/2000 | Hahn | |
| 6,391,864 B1 | 5/2002 | Stone | |
| 6,432,929 B1 | 8/2002 | Stone | |
| 6,607,745 B2 | 8/2003 | Leneau | |
| 6,875,753 B1 | 4/2005 | Pilarski | |
| 6,924,273 B2 | 8/2005 | Pierce | |

(Continued)

FOREIGN PATENT DOCUMENTS

CA    2 156 013 A    2/1997

(Continued)

OTHER PUBLICATIONS

Brown et al., *The Lancet*, vol. 343, pp. 831-836 (Apr. 1994).

(Continued)

*Primary Examiner* — Michael G. Wityshyn
*Assistant Examiner* — T. E. Underdahl
(74) *Attorney, Agent, or Firm* — Birch, Stewart, Kolasch & Birch, LLP

(57) ABSTRACT

The invention discloses the discovery that a pharmaceutical composition containing complex carbohydrates with or without natural or synthetic essential oils can work effectively as a topical, oral or mucosal pharmaceutical composition. Such pharmaceutical compositions reduce inflammation, assist in wound healing, protect against bruising, relieve itching, relieve pain and swelling and treat topical bacterial infections such as acne and decubitus ulcers and prevent and treat numerous other conditions and diseases. Such pharmaceutical compositions can be administered to mammals including humans. Also included in this invention are methods to deliver topically applied macromolecules into the tissue of mammals and methods of blocking the adhesion, metastatic and coronary cascades.

65 Claims, No Drawings

U.S. PATENT DOCUMENTS

| | | |
|---|---|---|
| 2002/0068718 A1 | 6/2002 | Pierce |
| 2004/0022847 A1 | 2/2004 | Leneau |

FOREIGN PATENT DOCUMENTS

| | | | |
|---|---|---|---|
| DE | 195 20 575 A1 | | 12/1996 |
| DE | 19520575 A1 | | 12/1996 |
| DE | 195 47 105 A1 | | 6/1997 |
| EP | 0 130 550 A2 | | 1/1985 |
| EP | 0 254 845 A2 | | 2/1988 |
| EP | 0444492 B1 | | 9/1991 |
| EP | 0 497 162 A1 | | 8/1992 |
| EP | 0 704 216 A1 | | 4/1996 |
| EP | 0 795 560 A1 | | 9/1997 |
| EP | 0 852 236 A1 | | 7/1998 |
| FR | 2674749 | | 10/1992 |
| JP | 59-163307 | * | 9/1984 |
| JP | S62-77308 | | 4/1987 |
| JP | 63-8309 | * | 1/1988 |
| JP | 01186824 | | 7/1989 |
| JP | 04 041431 A | | 2/1992 |
| JP | 06 107550 A | | 4/1994 |
| JP | 06107550 A | | 4/1994 |
| JP | 9-262057 | * | 10/1997 |
| WO | WO 90/00058 A1 | | 1/1990 |
| WO | WO 92/18546 A1 | | 10/1992 |
| WO | WO 92/22585 A1 | | 12/1992 |
| WO | WO 93/05075 A1 | | 3/1993 |
| WO | WO 93/09766 A1 | | 5/1993 |
| WO | WO 9309766 | | 5/1993 |
| WO | 9311780 | | 6/1993 |
| WO | WO 93 11780 A | | 6/1993 |
| WO | WO 95/23605 A1 | | 9/1995 |
| WO | WO 9531177 | | 11/1995 |
| WO | WO 95/34286 A1 | | 12/1995 |
| WO | WO 96/05845 A3 | | 2/1996 |
| WO | WO 96/32492 A1 | | 10/1996 |
| WO | WO 97/25051 | * | 7/1997 |
| WO | WO 97/25051 A1 | | 7/1997 |
| WO | WO 97/33592 A1 | | 9/1997 |
| WO | WO 97/40841 A1 | | 11/1997 |
| WO | WO 97/45435 A1 | | 12/1997 |
| WO | WO 98/06730 A1 | | 2/1998 |
| WO | WO 98/08854 A2 | | 3/1998 |

OTHER PUBLICATIONS

Shimizu et al., *Journal of Immunology*, vol. 143, pp. 2457-2463, No. 8 (Oct. 1989).
Munro et al., *American Journal of Pathology*, vol. 141, No. 6, pp. 1397-1408 (Dec. 1992).
Lawrence et al., *Progress in Essential Oils, Perfumer & Flavorist*, vol. 17, pp. 51-60 (Nov./Dec. 1992).
Elkhouly et al., *Australian Journal of Pharmaceutical Sciences*, vol. 9, pp. 81-84 (Sep. 1980).
Ibrahim, *Pharm. Acta Helv.*, vol. 66, pp. 286-288 (1991).
Williams et al., *International Journal of Pharmaceutics*, vol. 57, R7-R9 (1989).
Yagi et al., *Journal of Pharmaceutical Sciences*, vol. 73, pp. 62-65, No. 1 (Jan. 1984).
Tyrrell et al., *Proc. Natl. Acad. Sci, USA*, vol. 88, pp. 10372-10376 (Nov. 1991).
Radin et al., *The Journal of Bone and Joint Surgery*, vol. 54-A, pp. 607-616 (Apr. 1972).
Howard et al., *The Compendium*, vol. 15, No. 3, pp. 473-479 (Mar. 1993).
*The Merck Index*, 11th Edition, pp. 735, 1072-1078 (1989).
Santus et al., *J. Controlled Release*, vol. 25, pp. 1-20 (1993).
Nelson et al., *Blood*, vol. 82(11), pp. 3253-3258 (1993) (Abstract Only).
Foxhall et al., *The Journal of Cell Biology*, vol. 117(4), pp. 895-902 (1992).
Tyrrell et al., *Proc. Natl. Acad. Sci. USA*, vol. 88, pp. 10372-10376 (1991).
Corbett, *Spec. Chem.*, vol. 11(7), pp. 493-494, 496, 501-502 (1991) (Abstract Only).
Collins & Ferrier, "Monosaccharides: Their Chemistry and Their Roles in Natural Products", (John Wiley & Sons), p. 4 (1995).
Ed. Sybil Parker, *McGraw-Hill Dictionary of Chemical Terms* (McGraw-Hill, Inc.), p. 278 (1984).
Lasky, *Annual Review of Biochemistry*, vol. 64, pp. 1B-139B (1995).
Dsaqupta & Tang, "Modern Synthetic Carbohydrate Chemistry", (ACS-Short Course, Aug. 19-20, 1994, Washington D.C.)
Office Action mailed Dec. 27, 2009 issued in copending U.S. Appl. No. 10/343,240, filed May 16, 2003.
Office Action mailed Jul. 31, 2006 issued in copending U.S. Appl. No. 10/343,240, filed May 16, 2003.
Office Action dated Aug. 7, 2007 in copending U.S. Appl. No. 10/343,240, filed May 16, 2003.
Office Action mailed Mar. 18, 2008 in copending U.S. Appl. No. 10/343,240, filed May 16, 2003.
Office Action mailed Jan. 26, 2009 in copending U.S. Appl. No. 10/343,240, filed May 16, 2003.
David C. Steinberg, *Cosmetic Technology*.—Mucopolysaccharides for cosmetics, (Feb. 1982), pp. 41-44.
Article: Essense Oils, 2 pages, DSH Perfumes 2004.
*Chemistry 470-"Industrial Chemistry"*, Spring 2004, Internet, 6 pages.
Srivas R. Srinivas, *Atlas of Essential Oils*, 2 pages, 1996.
D. Kobayashi et al., *Pharmaceutical Research*, vol. 11, No. 1, 1994, Analysis of the Combined Effect of 1-Menthol and Ethanol as Skin Permeation Enhancers Based on a Two-Layer Skin Model (article), received Dec. 4, 1992—accepted Jun. 22, 1993; pp. 96-103.
Hans Schaefer et al., *Skin Barrier* (article), 3 pages, Karger, 1996.
Claire Parisel et al., Interactions of heparin with human skin cells: Binding, location, and transdermal penetration (article); Received Nov. 5, 2002, Accepted Mar. 4, 2003; pp. 517-523; 2003 Wiley Periodicals, Inc.
Pankaj Karande et al., , *Nature Biotechnology-Advance Online Publication*, Discovery of transdermal penetration enhancers by high-throughput screening (article), published online (Jan. 4, 2004), pp. 1-6.
Gregory M. Glenn et al., *Nature* vol. 391, Skin immunization made possible by cholera toxin (article), (Feb. 26, 1998), 1 page.
Gregory M. Glenn et al., *Cutting Edge*, Cutting Edge: Transcutaneous Immunization with Cholera Toxin Protects Mice Against Lethal Mucosal Toxin Challenge (artilcle), pp. 3211-3214, 1998.
Tanya Scharton-Kersten et al., *Infection and Immunity*, vol. 68, No. 9, Transcutaneous Immunization with Bacterial ADP-Ribosylating Exotoxins, Subunits, and Unrelated Adjuvants (Sep. 2000), pp. 5306-5313.
Gregor Cevc et al., *Biochimica et Biophysica Acta*, vol. 1368, (1998), Ultraflexible vesicles, Transfersomes, have an extremely low pore penetration resistance and transport therapeutic amounts of insulin across the intact mammalism skin, pp. 201-215.
Raghavachari et al., *Journal of Pharmaceutical Sciences*, vol. 91, No. 3, (Mar. 2002), Targeted Gene Delivery to Skin Cells in Vivo: A Comparative Study of Liposomes and Polymers as Delivery Vehicles, 9 pages.
Marc Cohen et al., *The Journal of Rheumatology*, vol. 30, No. 3, (2003) A Randomized, Double Blind, Placebo Controlled Trial of a Topical Cream Containing Glucosamine Sulfate, Chondroitin Sulfate, and Camphor for Osteoarthritis of the Knee, pp523-528.
*Marie Curie and the Science of Radioactivity*—Research Breakthroughs (1897-1904) 2 pages; *2000-2004 American Institute of Physics*.
*Naturopathic Laboratories International, Inc.*, Plaintiff, v. *Dermal Research Laboratories, Inc.*, Defendant, Complaint, 8 pages, U.S. District Court for the Western District of Missouri Western Division, 2006.
*Naturopathic Laboratories International, Inc.*, Plaintiff, v. *Dermal Research Laboratories, Inc.*, Defendant, Dermal Research Laboratories, Inc.'s Answer and Counterclaim to Naturopathic Laboratories International Inc.'s Complaint, 14 pages, U.S. District Court for the Western District of Missouri Western Division, 2006.
*Naturopathic Laboratories International, Inc.*, Plaintiff, v. *Dermal Research Laboratories, Inc.*, Defendant, Reply of Naturopathic Laboratories International, Inc., to Counterclaim of Dermal Research Laboratories, Inc., 6 pages, U.S. District Court for the Western District of Missouri Western Division, 2006.
*Naturopathic Laboratories International, Inc.*, Plaintiff, v. *Dermal Research Laboratories, Inc.*, Defendant, Plaintiff Naturopathic Laboratories, International, Inc.'s Response to Defendant's First Set of Interrogatories, 14 pages, U.S. District Court for the Western District of Missouri Western Division, 2006.
David C. Steinberg, Report, 25 pages, 2004.
Dr. Karen K. Brown, Notes: D000459 and D000460; Jan. 9, 1992 & Jan. 18, 2002; 2 pages.
*Naturopathic Laboratories International, Inc.*, Plaintiff, v. *Dermal Research Laboratories, Inc.*, Defendant, Expert Rebuttal to the Invalidity Report of Mar. 8, 2004, Regarding United States Patent No. 5,888,984, Apr. 9, 2004, 27 pages.
The 1998 CIR Expert Panel Members: Chairman Wilma Bergfeld, MD, FACP, Donald Belsito, MD, William Cariton, PhD., DVM. Curtis Klaassen, PhD., Arnold L. Schroeter, MD, and Ronald C. Shank, PhD., and Thomas Saga, PhD, Cir Director: f. Alan Andersen, PhD, *Final Report: Safety Assessment of Peppermint*, Sep. 11, 1998, 18 pages, *Cosmetic Ingedient Review*—Washington, DC.
*Naturopathic Laboratories International, Inc.*, Plaintiff, v. *Dermal Research Laboratories, Inc.*, Defendant, Claim Construction of '984 Patent; Jan. 23, 2004; 11 pages; U.S. District Court for the Western District of Missouri Western Division.
*Naturopathic Laboratories International, Inc.*, Plaintiff, v. *Dermal Research Laboratories, Inc.*, Defendant, Suggestions in Support of Dermal Research Laboratories, Inc.'s Motion for Summary Judgment on Naturopathic Laboratories International, Inc.'s Invalidity Defenses; Jun. 7, 2004; 27 pages; U.S. District Court for the Western District of Missouri Western Division.
*Naturopathic Laboratories International, Inc.*, Plaintiff, v. *Dermal Research Laboratories, Inc.*, Defendant, Deposition of Harold Brown, PhD, Feb. 26, 2004; 335 pages (copies in quarters); U.S. District Court for the Western District of Missouri Western Division.
*Naturopathic Laboratories International, Inc.*, Plaintiff, v. *Dermal Research Laboratories, Inc.*, Defendant, Deposition of Karen Brown, Ph.D.; Oct. 23, 2003; 335 pages (copies in quarters); U.S. District Court for the Western District of Missouri Western Division.
*Naturopathic Laboratories International, Inc.*, Plaintiff, v. *Dermal Research Laboratories, Inc.*, Defendant, Deposition of Carol Cooper, Ph.D.; Feb. 17, 2004; 339 pages (copied in quarters); U.S. District Court for the Western District of Missouri Western Division.
David C. Steinberg, *Cosmetic Technology*. Mucopolysaccharides for cosmetics, (Feb. 1982), pp. 41-44.

Article: Essence Oils, 2 pages DSH Perfumes 2004.
*Chemistry 470- "Industrial Chemistry"*, Spring 2004, Internet, 6 pages.
Srivas R. Srinivas, *Atlas of Essential Oils*, 2 pages. 1996.
D. Kobayashi et al., *Pharmaceutical Research*, vol. 11, No. 1, 1994, *Analysis of the Combined Effect of 1-Menthol and Ethanol as Skin Permeation Enhancers Based on a Two-Layer Skin Model* (article), received Dec. 4, 1992—accepted Jun. 22, 1993; pp. 96-103.
Hans Schaefer et al.; *Skin Barrier* (article), 3 pages, Karger 1996.
Claire Parisel et al., *Interactions of heparin with human skin cells: Binding, location, and transdermal penetration*(article); Received Nov. 5, 2002, Accepted Mar. 4, 2003; pp. 517-523; 2003 *Wiley Periodicals, Inc.*
Pankaj Karande et al., *Mature Biotechnology-Advance Online Publication, Discovery of transdermal penetration enhancers by high-throughout screening*(article), published online (Jan. 4, 2004), pp. 1-6.
Gregory M. Glenn et al., *Nature* vol. 391, *Skin immunization made possible by cholera toxin*(article), (Feb. 26, 1998), 1 page.
Gregory M. Glenn et al., Cutting Edge, *Cutting Edge: Transcutaneous Immunization with Cholera Toxin Protects Mice Against Lethal Mucosal Toxin Challenge*(article), pp. 3211-3214. 1998.
Tanya Scharton-Kersten et al., *Infection and Immunity*, vol. 68, No. 9, *Transcutaneous Immunization with Bacterial ADP-Ribosylating Exotoxins, Subunits, and Unrelated Adjuvants*(Sep. 2000), pp. 5306-5313.
Gregor Cevc et al., *Biochimica et Biophysica Acta*, vol. 1368, (1998), *Ultraflexible vesicles, Transfersomes, have an extremely low pore penetration resistance and transport therapeutic amounts of insulin across the intact mammalism skin*, pp. 201-215.
Raghavachari et al., *Journal of Pharmaceutical Sciences*, vol. 91, No. 3, (Mar. 2002), *Targeted Gene Delivery to Skin Cells In Vivo: A Comparative Study of Liposomes and Polymers as Delivery Vehicles*, 9 pages.
Marc Cohen et al., *The Journal of Rheumatology*, vol. 30, No. 3, (2003) *A Randomized, Double Blind, Placebo Controlled Trial of a Topical Cream Containing Glucosamine Sulfate, Chondroitin Sulfate, and Camphor for Osteoarthriitis of the Knee*, pp. 523-528.
*Marie Curie and the Science of Radioactivity—Research Breakthroughs* (1897-1904) 2 pages; 2000-2004 *American Institute of Physics*.

* cited by examiner

PHARMACEUTICAL COMPOSITION OF COMPLEX CARBOHYDRATES AND ESSENTIAL OILS AND METHODS OF USING THE SAME

This application is the national phase under 35 U.S.C. §371 of PCT International Application No. PCT/US00/02328 which has an International filing date of Feb. 1, 2000, which designated the United States of America and was published in English.

The contents of Provisional applications U.S. Ser. Nos. 60/117,988, 60/127,749, 60/137,098, 60/142,306 and 60/166,326 filed on Feb. 1, 1999, Apr. 5, 1999, Jun. 2, 1999, Jul. 3, 1999 and Nov. 19, 1999, respectively on which the present application is based and benefit is claimed under 35 USC 119(e) is herein incorporated by reference.

BACKGROUND AND FIELD OF THE INVENTION

The invention relates to a method of preventing and treating diseases and conditions of mammals associated with the adhesion, metastatic and coronary cascades comprising applying a composition of complex carbohydrates and essential oils topically, orally or mucosally on a repeated basis. The invention also encompasses a method of preventing and treating diseases and conditions associated with the adhesion, metastatic and coronary cascades comprising orally or mucosally applying complex carbohydrates as the sole active ingredient.

Complex carbohydrates, for purposes of this invention are defined as any polymer comprising more than two sugar moieties including such classes of compounds as polysaccharides and oligosaccharides. Polysaccharides include mucopolysaccharides and mannans whereas oligosaccharides are comprised of branched polysaccharides such as sialylated sugars including milk sugars.

Mucopolysaccharides are glycosaminoglycans which can be obtained from numerous sources (e.g. rooster combs, trachea, umbilical cords, skin, articular fluids and certain bacteria such as *Streptococci* spp). Most glycosaminoglycans (hyaluronic acid, chondroitin sulfates A, B, and C, heparin sulfate, heparin, keratan sulfate, dermatan sulfate, etc.) are composed of repeating sugars such as n-acetylglucosamine, glucuronic acid and n-acetyl galactosamine (these are known as non-sulfated glycosaminoglycans). If such glycosaminoglycans contain sulfur groups they are known as sulfated glycosaminoglycans.

Mannans are mannose-based polysaccharides which are normally extracted from plants. The most noteworthy is acemannan which is a beta 1,4-linked acetylated mannan extracted from the Aloe Vera plant (Aloe barbadensis Miller). This plant has been thought for centuries to have certain healing powers. Not until the 1980s was the active ingredient isolated and proven to have an effect on the immune system (see J. Pharm. Sci., 73 (1), January, 1984). Sialylated sugars are oligosaccharides which contain sialyl groups (e.g. sialic acid) and often contain fucose. Sialyl Lewis$^x$ and its derivatives are examples from this group (Tyrell et al, Proc. Natl. Acad. Sci. USA, 88, November 1991). At present, this oligosaccharide is so difficult to prepare/obtain that the cost is prohibitive and limits research activities to determine its mechanism of action. Some of the milk sugars (also called hexaoses) are also incorporated in this general class of compounds. Examples of these are difucosyllacto-N-hexaose a and b, Disialyl-monofucosyllacto-N-hexaose and monofucosyllacto-N-hexsaose I, II, and II (obtainable from Oxford Glycosystems, Inc.).

Heparin, hyaluronic acid and chondroitin sulfate are the most studied complex carbohydrates. They fall in the class called mucopolysaccharides or glycosaminoglycans. Heparin has been used for a number of years as an anticoagulant. Hyaluronic acid has been used therapeutically since the 1970s as a replacement for the vitreous humor of the eye post surgery and, more recently, as replacement for joint fluid in arthritic joints. An extensive discussion of its various utilities is found in U.S. Pat. No. 4,141,973 to Balazs. The mode of action for hyaluronic acid injected directly into joints for treatment of arthritis has been proposed to be lubrication and replacement of the degraded joint fluid with highly viscous hyaluronic acid (see J. Bone Jt. Surg. 54A, 1972). High molecular weight (>1,000,000 daltons) and high viscosity have been reported to be critical. (For purposes of this application, all molecular weights are expressed as daltons. The unit designation will not be added hereafter.)

In the 1980s, it was discovered that chondroitin sulfate, or polysulfated glycosaminoglycan (known by its commercial name as ADEQUAN) could be injected intramuscularly for reduction of pain and inflammation associated with arthrosis of horses. The mechanism of action of this glycosaminoglycan has been speculated to be inhibition of certain degradative enzymes present in the joint fluid which are up-regulated by trauma.

In the 1990s, chondroitin sulfate had developed into a popular nutritional supplement being used extensively to treat joint disease. Such treatment requires oral doses between 1000 and 3000 mg/day of for humans. Even with these high doses, relief from joint pain often takes 6-9 months.

In 1989, it was discovered that intravenous, intramuscular or subcutaneous delivery of hyaluronic acid could reduce the pain of arthritis (U.S. Pat. No. 4,808,576 by Schultz et al) when the hyaluronic acid was delivered remote to the site of the arthritis (not into the joint). This patent specifically states that the hyaluronic acid is administered remote to the site and that the hyaluronic acid must be of high purity (>99% pure hyaluronic acid). Schultz et al. does not disclose or suggest the use of hyaluronic acid in combination with essential oils, use of other complex carbohydrate macromolecules, oral application or mucosal application. Schultz et al. specifically teaches away from use of low purity complex carbohydrates. By low purity is meant complex carbohydrates that would be considered food grade or cosmetic grade, which could be <98% pure and could contain such contaminants as endotoxins, lipoteichoic acids, proteins, nucleic acids, etc. The low purity hyaluronic acid or salt thereof useful in the present invention (<98% pure hyaluronic acid) can be of a cosmetic grade or food grade which can contain up to 5% contaminants. Such material would not pass the owl monkey eye test used to select high purity hyaluronic acids and salts thereof (described by Balazs in U.S. Pat. No. 4,141,973) in that it would produce an inflammatory response (e.g. inflammatory reaction) in the eye. It also would not pass the horse joint injection test described by Schultz et al (U.S. Pat. No. 4,808,576). However, it does not produce a reaction when applied to the skin or mucous membranes of mammals including humans, dogs, cats, horses, cattle, swine, rabbits, guinea pigs and mice.

The importance of high molecular weight for effectiveness of hyaluronic acid in the treatment of arthritis is emphasized by Balazs (U.S. Pat. No. 4,141,973) and in a publication by Howard and McIlraith (see The Compendium, 15(3), March 1993) who summarize several clinical studies conducted to determine the most efficacious molecular weight range of hyaluronic acid injected intra-articularly to treat traumatic arthritis in horses. The conclusion from these studies is that hyaluronic acid with a molecular weight below $1 \times 10^6$ is not as effective as hyaluronic acid with a molecular weight above this value. More recently, della Valle et al (U.S. Pat. No. 5,166,331) claimed that there are two distinct pharmacologically active molecular weight ranges of hyaluronic acid or salts thereof. These moieties are utilized separately (purified one from the other) and defined as 50,000-100,000 (Hylastine) and 500,000-730,000 (Hylectin). Hylastine is specified for use in wound healing while Hylectin is specified for use in ocular surgery.

Whereas Balazs (U.S. Pat. No. 4,141,973), Schultz (U.S. Pat. No. 4,808,576) and della Valle (U.S. Pat. No. 5,166,331) all specify use of highly purified hyaluronic acid and whereas Balazs (U.S. Pat. No. 4,141,973) discards the fractions containing hyaluronic acid or their salts having molecular weights less than 750,000; and whereas della Valle (U.S. Pat. No. 5,166,331) discards impurities having molecular weights less than 30,000 and does not use hyaluronic acid with molecular weights between 100,000 and 500,000 and, thus, specifies use of clearly-defined molecular weights of hyaluronic acid for topical or ocular use; and whereas Schultz prefers use of hyaluronic acid with a molecular weight between $1.2 \times 10^6$ and $4.0 \times 10^6$ in topical formulations, we have discovered that all molecular weights of complex carbohydrates such as hyaluronic acids or salts thereof and all purities of these compounds are useful in topical, oral or mucosal preparations for the treatment of numerous diseases and conditions.

The most recent studies on hyaluronic acid discuss treatment of various types of cancer with very large doses of this macromolecule (Falk, WO 97/40841). The Falk application suggests that doses should exceed 750 mg. per 70 kg person, preferably, exceeding 1 g. per 70 kg person. Such doses are given intermittently post diagnosis and are not suggested to be preventative or administered in low doses. Additionally, it is clear that the sodium hyaluronate of Falk needs to be pure enough for injection even though oral administration is used in addition to intravenous injection.

Essential oils are natural components of plants and animals that are extracted by various methods known to the art. They are generally very complex, containing numerous compounds (see Perfumer and Flavorist, 17, November/December 1992). More recently, some of the essential oils have been chemically synthesized. Most uses of these oils are as flavorings for foods and candies and as bath, cosmetic and perfume ingredients to provide pleasant aromas. Several of the essential oils (i.e. Menthol, Eucalyptus Oil, Camphor, Peppermint Oil and Wintergreen Oil) are currently used in over-the-counter topical preparations such as BenGay, Mineral Ice, Flexall 454, etc. at concentrations as high as 50%. These topical medications claim pain relief but, according to FDA, act to relieve pain by producing a counterirritation, not by penetrating the skin and acting systemically to reduce inflammation and swelling which are the causes of pain.

The Adhesion Cascade was first described in the early 1990s. In a summary by Adams and Shaw (The Lancet, 343, Apr. 2, 1994) the adhesion cascade which is stimulated when trauma occurs is divided into four sequential steps of tethering, triggering, strong adhesion and motility. Tethering interactions are mediated by a family of three lectin-like carbohydrate-binding molecules (selectins). These interactions are strong enough to cause the leukocytes to roll along the blood vessel walls to the site of trauma instead of flowing freely through such vessels, but not strong enough to cause these leukocytes to slow down. The triggering response is stimulated by factors such as cytokines and mediated by adhesion molecules called integrins. Integrins, by themselves, do not bind well to epithelium. However, when activated, integrins promote strong adhesion of the leukocyte to the epithelial surface. Leukocytes bind to the epithelial cells via their receptor sites such as CD44, CD31, etc. During strong adhesion, the interaction of these integrins with their ligands on the surface of the leukocytes are responsible for cessation of movement and flattening of the leukocyte. Finally, a process involving VCAM-1 and LFA-1 and other such integrins allows leukocytes to pass between endothelial cell junctions and into the tissue that has been traumatized. Collection of leukocytes at the site of trauma produces inflammation which is then followed by pain or other sequelae.

The present invention is based upon the premise that complex carbohydrates, including but not limited to glycosaminoglycans, bind to the receptor sites on leukocytes blocking their ability to tether to the blood vessel walls thus inhibiting the motility and interrupting the Adhesion cascade.

The metastatic cascade is very similar to the adhesion cascade. It has been proposed that tumor cells of all types contain CD44 receptor sites on their surface. These CD44 receptor sites appear to be involved in metastasis functioning similar to the receptor sites on leukocytes—tethering the tumor cells to the blood vessel wall and providing the motility necessary for movement from one site to another in the mammalian body. Once again, it is the premise of the present invention that complex carbohydrates, including but not limited to glycosaminoglycans, bind to the receptor sites on tumor cells blocking their ability to tether to the blood vessel walls and inhibiting the motility which, in turn, interrupts the potential for metastasis.

A Coronary cascade has recently been described in the Harvard Health Letter (December 1999, pg. 4-5). This cascade leads to the development of heart disease and stroke by causing plaque formation in the blood vessels. The theory is based on the premise that there are stable and unstable plaques produced on blood vessel walls. Unstable plaques are "swarming with T cells and macrophages" causing inflammation and make these plaques unstable. The T cells are described as sending macrophages a signal to release a protein called tissue factor which "spills out and encounters circulating blood, attracting platelets and triggers formation of a clot that quickly blocks up the artery". The compositions of the present invention are believed to inhibit the macrophages from infiltrating into the unstable plaques, thus preventing and treating heart disease and stroke.

It is unexpected that complex carbohydrates of the present invention could be administered topically, orally or mucosally in low doses to inhibit the various cascades preventing and treating such a broad spectrum of diseases and conditions.

OBJECTS AND SUMMARY OF THE INVENTION

Although not bound by any theory, the invention relates to a method of preventing and treating diseases associated with the Adhesion and Metastatic cascades comprising applying a composition of complex carbohydrates and essential oils topically, orally or mucosally on a repeated basis. The invention also encompasses a method of preventing and treating diseases associated with the Adhesion and Metastatic cascades comprising mucosally applying complex carbohydrates as the sole active ingredient.

More specifically, this invention describes a mechanism by which inflammation, including diseases and conditions associated therewith, tumor growth, tumor metastasis and/or allergies and allergy-related diseases can be prevented or treated.

It is understood that this invention describes the prevention and treatment of numerous diseases and conditions including but not limited to arthritis (osteoarthritis and rheumatoid arthritis), gastritis, colitis, esophagitis, bronchitis, sore throat, tonsilitis, tendonitis, fibromyalgia, sunburn, heat burns, temporomandibular joint (TMJ) condition, dental pain, itching associated with allergies and hypersensitivity, poison ivy, asthma, anaphylaxis, Attention Deficit Hyperactivity Disorder (ADHD), plaque formation associated with heart disease and stroke, increased degradation of spinal nerves post spinal cord injury, adhesion formation post surgery, scar formation post surgery, wound healing, decubutis ulcers, ganglion formation, Alzheimer's disease, HIV, cancer, Diabetes, skin problems such as acne, psoriasis, wrinkles, and even hair loss.

Such prevention and treatment are accomplished by topically, orally or mucosally applying complex carbohydrates with or without essential oils to mammals in an amount and number of applications so as to be effective in preventing and treating the target disease or condition. It is proposed that such prevention or treatment results from blockage of the Adhesion, Metastatic, or Coronary cascades.

The delivery of these compounds to the site of trauma is accomplished by topical application of said compounds whereby the compounds are combined with essential oils, by oral delivery of said compounds whereby the compounds are mixed with essential oils, coated with protective oral delivery materials such as hydrogels, carbopols, etc., or delivered without a coating wherein the complex carbohydrates are the sole active ingredients (e.g. without the essential oil(s) being present as an active ingredient), and/or delivered mucosally wherein the complex carbohydrates are the sole active ingredients (e.g. without the essential oil(s) being present as an active ingredient).

Mucosal delivery includes but is not limited to application of the compounds to the mucous membranes of the nose, eyes, mouth, throat, gums, tonsils, eyes, esophagus, stomach, colon, rectum, vagina, or any other mucous membrane.

It is a further advantage of this invention that ultrapure or purified complex carbohydrates do not need to be used. Therefore, cosmetic or food grade complex carbohydrates, are acceptable for use to prevent or treat the above diseases or conditions if they are applied topically, orally or mucosally. The preferred complex carbohydrates of this invention are mucopolysaccharides (glycosaminoglycans) including hyaluronic acid and salts, sulfates or derivatives thereof, chondroitin sulfate and polysulfated forms, salts or derivatives thereof, sialyl Lewis$^x$ and salts or derivatives thereof, heparin and sulfates, salts or derivatives thereof, dermatan, and sulfates, salts or derivatives thereof, keratin and salts, sulfates and derivatives thereof, as well as combinations of the above. The most preferred complex carbohydrates are hyaluronic acid including salts, sulfates, esters, or derivatives thereof, chondroitin sulfate including polysulfated forms, low molecular weight heparin including salts, sulfates and derivatives thereof and sialyl Lewis$^x$ including salts and derivatives thereof and combinations of the above.

It is an additional discovery that all sizes of complex carbohydrates are effective in this invention. Therefore, glycosaminoglycans, including chondroitin sulfate, heparin and hyaluronic acids of molecular weights <1,000, between 500,000 and 4,000,000, as well as above 4,000,000 are effective and non-reactive.

It is a further discovery that essential oils can be used to topically, orally or mucosally deliver macromolecules (molecules with a molecular weight >1000) into the dermal tissue and, consequently, into the blood stream or to deliver said macromolecules mucosally. Additionally, it is a discovery that said macromolecules can be absorbed mucosally without the assistance of a delivery system and that said mucosally-absorbed macromolecules are effective at low doses.

Finally, it has been discovered that the Adhesion cascade which when stimulated by trauma, an allergen or other trigger mechanism which results in build up of leukocytes at the site of trauma or the trigger site can be blocked by delivering the complex carbohydrates of this invention according to the methods of this invention.

Therefore, it has unexpectedly been found that essential oils when formulated with complex carbohydrates including polysaccharides, oligosaccharides, sialylated sugars, glycosaminoglycans or even monoclonal antibodies specific for the Adhesion or Metastatic cascades, can effectively treat the above-mentioned diseases and conditions when applied topically, orally, or mucosally.

Neither the complex carbohydrates nor the essential oils alone, when administered topically (e.g. topically as used in the present application does not include orally or mucosally) on the site of pain and inflammation, produce a significant preventative or therapeutic effect. However, when combined in the mixtures described herein, there is a definite therapeutic effect which can be felt within 30 minutes of the application.

Even more unexpectedly, it has been discovered that the complex carbohydrates alone can be applied orally or mucosally without essential oils to obtain an even better response (prevention or treatment) with a smaller dose.

This invention also describes a composition of matter comprising at least one complex carbohydrate and at least one essential oil and also the method for effecting transdermal migration resulting in topical delivery of compounds, including macromolecules, through the skin of mammals and into the bloodstream by combining such compounds with essential oils.

This invention also encompasses a composition of matter comprising complex carbohydrate macromolecules as the sole active ingredient (e.g. without the essential oil(s) being present as an active ingredient), applied orally or mucosally to inhibit the Adhesion, Metastatic or Coronary cascades thus preventing or treating numerous diseases and conditions related thereto.

Macromolecules as used herein means any molecule with a molecular weight >1000. Mammals as used herein includes humans, dogs, cats, horses, cattle, swine, rabbits, guinea pigs, mice, and all other mammalian animals.

DETAILED DESCRIPTION OF THE INVENTION

As discussed above, there have been no previous investigations describing use of complex carbohydrates in combination with essential oils to prevent and/or treat diseases and conditions associated with the Adhesion, Metastatic and Coronary cascades. There have also been no previous investigations describing use of complex carbohydrates as the sole active ingredient (e.g. without the essential oil(s) being present as an active ingredient) to prevent and treat diseases associated with the Adhesion, Metastatic and Coronary cascades when delivered orally or mucosally, especially in low doses. By low doses is meant from 0.00005 mg/kg to 50 mg/kg, preferably from 0.005 mg/kg to 40 mg/kg, more preferably from 0.05 mg/kg to 20 mg/kg.

The diseases and conditions that are preventable or treatable according to this invention (e.g. composition using the present active ingredient (complex carbohydrate) with or without essential oil(s)) include but are not limited to arthritis (osteoarthritis and rheumatoid arthritis), gastritis, colitis, esophagitis, bronchitis, sore throat, tonsilitis, tendonitis, fibromyalgia, headaches including migraines, pancreatitis, vaginitis, hemorrhoids, sunburn, heat burns, TMJ, dental pain, gingivitis, dental caries, post surgical pain, menstrual pain, anaphylaxis, pain prior to and during childbirth, itching associated with allergies and hypersensitivity, poison ivy, asthma, Attention Deficit Hyperactivity Disorder (ADHD), plaque formation associated with heart disease and stroke, increased degradation of spinal nerves post spinal cord injury, adhesion formation post surgery, scar formation post surgery, lack of wound healing, decubitus ulcers, irritation of nerve bundles, ganglion formation, Alzheimer's disease, HIV, cancer, Diabetes, skin problems such as acne, psoriasis, wrinkles, and even hair loss.

The invention also describes a process for reducing the sequelae of trauma in irritated or inflamed tissue of mammals by the topical application of a mixture of an essential oil or oils and a complex carbohydrate or mixture thereof. The pharmaceutical composition described is applied directly on or over the traumatized site.

Finally, the invention describes a process for reducing the sequelae of trauma in irritated or inflamed tissue of mammals by oral or mucosal application of a complex carbohydrate or mixture thereof as the only active ingredient (e.g. without the essential oil(s) being present as an active ingredient).

Particularly amenable conditions for such prevention or treatment include but are not limited to irritated or inflamed muscles, cramped muscles, inflamed tendons, fibromyalgia, swollen and painful joints, bruised tissue, tired feet, allergic conditions of the skin, other allergic conditions including psoriasis, asthma, anaphylaxis, ADHD, open wounds, decubitis ulcers, burns, sunburns, inflamed stomach or intestinal lining (gastritis, colitis), dental problems, inflamed bronchi or esophagial lining, inflamed nerve bundles (ganglia), adhesions formed after surgery or trauma, post surgical pain, pain during and after childbirth, plaques formed on veins or arteries leading to heart disease and stroke, inflammation associated with Alzheimer's Disease, tumor formation and tumor metastasis.

A significant advantage of this invention is that pharmaceutical grade complex carbohydrates are not required. The invention preferably uses cosmetic or food grade complex carbohydrates. Such complex carbohydrates can be obtained from any source as long as the source is not contaminated with undesirable adventitious agents (disease-producing viruses, bacteria, fungi, parasites, etc.). For instance, cosmetic grade hyaluronic acid which is of low purity (containing up to 5% impurities such as proteins, nucleic acids, teichoic acids and endotoxins) costs approximately $2,000/Kg, whereas high purity pharmaceutical grade hyaluronic acid required for injection into mammals costs at least $100,000/Kg and contains less than 0.5% impurities. Low purity complex carbohydrates such as mucopolysaccharides may be contaminated with up to 5% wt/vol proteins, 5% wt/vol nucleic acids, 1% wt/vol teichoic acids, 5% wt/vol lipids, fractions of hyaluronic acid <30,000 (defined as reactive by both Balazs in U.S. Pat. No. 4,141,973 and della Valle in U.S. Pat. No. 5,166,331), 5% wt/vol endotoxins and other small molecules. Preferably "low purity" means containing up to about 5% impurities, more preferably from about 0.6-5% impurities, still more preferably from about 1-5% impurities. They will cause reactions when injected into monkey eyes or joints of horses but will not cause reactions when applied to the skin of mammals or when delivered orally or mucosally to such mammals. Because the pharmaceutical compositions of this invention are applied topically, orally or mucosally, these contaminants produce no adverse reactions (e.g. irritation or blistering of skin). Additionally, if one must select and use only certain molecular weight ranges of hyaluronic acid or salts thereof, the cost would be prohibitive. In fact, the presence of multiple molecular weight fractions in compositions of the present invention is preferable for the efficacy.

In order to assure freedom from contaminating microorganisms, the formulations of this invention can include preservatives allowable in foods or topical preparations. Allowable preservatives include but are not limited to methyl and propyl parabens, propylene glycol, ethylenediamine tetraacetic acid (EDTA), sorbitol, ascorbic acid, sorbate and sorbic acid, benzoic acid, and any other acceptable preservative, including mixtures thereof. Preservatives that would not be allowable in oral or mucosal formulations include those that are know carcinogens such as formaldehyde, phenol, glutaraldehyde, and alcohols that are toxic to mammals (e.g. isopropyl, propyl, denatured alcohol).

All molecular weight ranges of complex carbohydrates are effective in formulations of this invention. For instance, hyaluronic acid with a molecular weight of <1,000, 1,000 to 30,000, 100,000-500,000, >1,000,000 or >4,000,000 have proven to be effective. It has been found that complex carbohydrates, especially glycosaminoglycans with lower molecular weights (e.g. <50,000, preferably <30,000) act more quickly than those with high molecular weights (e.g. >1,000,000). However, the high molecular weight glycosaminoglycans provide a longer-lasting effect. It is believed that the latter macromolecules are broken down by enzymes in the body to smaller molecules. Therefore, there is a longer release of the more active smaller molecules producing a longer period of efficacy. Therefore, the preferred formulation includes a mixture of low and high molecular weight complex carbohydrates.

The complex carbohydrates useful in combination with essential oils for direct topical application on sites of trauma may be of any type already recognized as useful for parenteral treatment. Additionally, complex carbohydrates, polysaccharides, glycosaminoglycans or their derivatives which bind to leukocyte receptor sites and/or bind to selectins, integrins, or any other receptor sites which are involved with the mechanism by which leukocytes move to sites of trauma or which enable metastasis of tumors and which, when bound, serve to inhibit any of the steps of the Adhesion or Metastatic cascades would be useful in such pharmaceutical compositions. Such compounds may be obtained from any source. They can be extracted from rooster combs (U.S. Pat. No. 4,141,973), produced by fermentation of bacteria (U.S. Pat. No. 4,782,046), or extracted from trachea, skin, umbilical cords, etc. and need only be pure enough to be used as a cosmetic in that they do not cause reactions when administered topically. These molecules include but are not limited to polysaccharides, glycosaminoglycans such as hyaluronic acids and derivatives or salts thereof (Genzyme, Lifecore Biomedicals, Meiji Seika Kaisha, Ltd.), chondroitin sulfates A, B, or C or their derivatives (SIGMA Chemical Company), keratan sulfate and derivatives thereof (SIGMA Chemical Company), heparin or heparin sulfate and derivatives thereof (SIGMA Chemical Company, Rhone Poulenc Rorer Pharmaceuticals), dermatan sulfate and derivatives thereof (SIGMA Chemical Company), mannans and derivatives thereof (SIGMA Chemical Company), acemannan (Carrington Laboratories) and derivatives thereof, extracts of the Aloe Vera plant and derivatives thereof (Aloe Vera gel concentrate supplied by Lily of the Desert, Irving, Tx.) and certain sialylated sugars such as trifucosyl-lacto-N-hexaose and sialyl Lewis$^x$ (Oxford Glycosystems). The sources listed are exemplary only and not limitations of the invention.

It is a preferred embodiment of this invention that at least two molecular weight ranges of complex carbohydrates be included in the pharmaceutical composition. At least one should be from a low molecular weight range {from 1000 to <50,000 (e.g. 49,000)} and the other one or more should be from a higher molecular weight range (from 100,000 to 500,000 or >1,000,000). Such complex carbohydrates may or may not be a mixture of two or more different types of complex carbohydrates. For instance, one complex carbohydrate providing the high molecular weight moiety could be selected from the group consisting of hyaluronic acid and mannans and another complex carbohydrate in the same pharmaceutical composition providing the low molecular weight moiety could be a second polysaccharide or a sialylated sugar selected from the group consisting of chondroitin sulfate, keratan sulfate, heparin, heparin sulfate, dermatan sulfate, acemannan, sialyl Lewis$^x$, and hexaoses.

A more preferred embodiment would comprise a mixture of at least two polysaccharides in the pharmaceutical composition. One of these polysaccharides would be of a low molecular weight range of <30,000 (e.g. 1000-29,000) and one polysaccharide would be of a high molecular weight >1,000,000. An even more preferred embodiment of this invention comprises a mixture of equal parts of at least two polysaccharides. One of the polysaccharides would be of a low molecular weight range (<30,000). The second polysaccharide would of be a high molecular weight hyaluronic acid or salt or derivative thereof (>1,000,000).

The most preferred embodiment of this invention comprises equal amounts of two or more molecular weight ranges of hyaluronic acid or salts or derivatives thereof. Such a composition would comprise for instance, a hyaluronic acid or salt or derivative thereof with a low molecular weight of <30,000 combined with a hyaluronic acid or salt or derivative thereof which has a high molecular weight >1,000,000.

When heparin is used, it is advantageous to use low molecular weight heparin as it has been demonstrated to be free of anti-coagulant activity. However, it is expected that high molecular weight heparin will be broken down to low molecular weight heparin when administered orally or mucosally.

When Aloe Vera is used to supply the complex carbohydrate, it is used as the base ingredient at a concentration of between 50% and 99% vol/vol Aloe Vera gel concentrate. A second complex carbohydrate such as a polysaccharide can be added to a concentration up to 5.0% wt/vol. This is then combined with an essential oil at a concentration of between 0.1% vol/vol and 20% vol/vol. The remaining portion of the formulation would be distilled deionized water (DI) and/or a cream or ointment base. A preferred embodiment comprises a 50% to 99% vol/vol Aloe Vera gel concentrate combined with a complex carbohydrate such as a polysaccharide at a concentration of between 0.01% and 5.0% wt/vol and an essential oil at a concentration of between 0.5% and 10.0% vol/vol. The remaining portion of the formulation would be DI water and/or a cream or ointment base. A more preferred embodiment of an Aloe Vera-containing formulation comprises 95% to 99% vol/vol Aloe Vera gel concentrate combined with hyaluronic acid at a concentration between 0.01% and 3.0% vol/vol and an essential oil at a concentration of between 0.5% and 5.0% vol/vol, the remainder being DI water. The most preferred embodiment of this formulation comprises a 98% vol/vol Aloe Vera gel concentrate (99% pure) as a base combined with high molecular weight hyaluronic acid at a concentration of between 0.1% and 1.0% vol/vol and an essential oil at a concentration between 1.0% and 3.0% vol/vol, the remainder being DI water. The essential oils would be selected from the group comprising Tea Tree Oil, Rosemary Oil, Oil of Wintergreen, Eucalyptus Oil, Camphor Oil and Menthol.

Unlike the essential oils used in current over-the-counter products and described in the above-mentioned publications, the essential oils used in this invention are incorporated into the formulation at minimal levels. The concentrations used are generally from 0.0001% to 20% vol/vol with a preferred embodiment containing from 0.5% to 10% vol/vol of such oils. A more preferred embodiment comprises a formulation containing a total concentration of 1.0% to 5.0% vol/vol essential oils. The most preferred embodiment comprises a formulation containing a total concentration of 1.0% to 3.0% vol/vol essential oils. The essential oils of the invention may be either natural or synthetic and may be obtained from any source. For instance, natural Eucalyptus Oil, Rosemary Oil, Pine Needle Oil, Tea Tree Oil, Sage Oil, Jojoba Oil, Cinnamon Oil, Anise Oil, Lemon Oil, Lime Oil, Orange Oil, Peppermint Oil, Spearmint Oil, Wintergreen Oil, Sweet Birch Oil, Clove Leaf Oil, Almond Oil, White Pine Oil, Camphor Oil, Cardamon Oil, Cedar Leaf Oil Sweet Birch Oil and many others can be purchased from Lorann Oils. Synthetic Wintergreen Oil, Anise Oil, Fir Tree Oil, Rose Oil and Camphor Oil can be obtained from the same source. Menthol and derivatives thereof can be obtained from SIGMA Chemical Company. The purity of these essential oils is of little concern as long as they meet the requirements for a cosmetic and do not produce adverse reactions when applied to the skin of mammals. An example of an animal-derived essential oil is EMU oil, extracted from the skin of the EMU.

For the purposes of this invention, the phrase "amount effective to allow penetration of the dermis of mammals" is preferably 0.1 to 20% vol/vol, more preferably 0.5 to 10% vol/vol and most preferably 1.0 to 5.0% vol/vol. The phrase "amount effective to allow penetration of the mucous membranes of mammals" is preferably 0.0001 to 0.09% vol/vol, more preferably 0.0001 to 0.01% vol/vol and most preferably 0.0001 to 0.001% vol/vol.

The formulation of a complex carbohydrate with a natural or synthetic essential oil should be adequate to form an emulsion, suspension, solution, cream or ointment at the time of application. A liquid formulation will not be effective if the oil is separated from the aqueous phase. However, a suspension or solution which may be resuspended by shaking prior to application is acceptable for use. Any cream or ointment base which does not interfere with the effectiveness of the active ingredients may be included in the formulation. Therefore, one embodiment of this invention is a cream base containing at least one complex carbohydrate and at least one essential oil. Another embodiment is an ointment base containing at least one complex carbohydrate and at least one essential oil. Yet another embodiment of the invention is an Aloe Vera base containing at least one complex carbohydrate and at least one essential oil. However, the preferred embodiment is a liquid formulation in an aqueous base which contains at least one complex carbohydrate and at least one essential oil. A significant advantage of this liquid formulation is that the preparation is not greasy or oily, does not leave a greasy or oily film on the skin and does not leave a lingering odor on the skin.

The treatment of irritated or inflamed mammalian tissue by direct topical application requires a dose or total dose regimen effective to reduce or alleviate the results of the trauma. It is preferred to administer at least about 0.000001 mg/lb of body weight of each ingredient over the site of trauma at least once per day or as often as necessary (e.g. 3 times per day, preferably 4 times per day, and most preferably 8 times per day, or simply "as needed"). The components of this formulation are naturally-occurring substances and are safe when applied topically. It is believed that there is no inherent upper limit to the tolerable dose. However, as in all medicinal treatments it is prudent to use no more than is necessary to achieve the desired effect. It has been noted that more intense inflammation and pain require more dose applications for relief. A dose of 100 mg/lb of body weight has been used safely and could serve as an upper limit for use. Similar dose regimens are recommended for wound healing whereas the pharmaceutical composition is applied on the wound until adequate promotion of granulation of the wound has occurred and healing is complete.

A convenient topical application formulation is a combination of one or more complex carbohydrates such as mannans, polysaccharides, oligosaccharides, or Aloe Vera extracts at a total concentration of between 0.1% and 99% wt/vol with one or more essential oils at a total concentration of between 0.5% and 20% vol/vol with the remainder of the formulation being made up of a liquid, cream or ointment base.

Another embodiment of the topical application formulation is a combination of one or more glycosaminoglycans at a total concentration of between 0.1% and 99% wt/vol with one or more essential oils at a total concentration of between 0.5% and 20% vol/vol with the remainder of the formulation being a cream, ointment or aqueous base.

Another embodiment of the topical application formulation is a combination of one or more mannans at a total concentration of between 0.1% and 99% wt/vol with one or more essential oils at a total concentration of between 0.5% and 20% vol/vol, the remainder being a cream, ointment or aqueous base.

A preferred embodiment of the invention is a combination of equal amounts of two or more complex carbohydrates of widely varying molecular weights (one below 30,000 and one above 500,000) at a combined concentration of between 0.5% and 3.0% wt/vol with two or more essential oils having a total concentration of between 0.5% and 5.0% vol/vol with the remainder of the formulation being an aqueous, cream or ointment base.

A more preferred embodiment of the topical application formulation is a combination of one or more glycosaminoglycans or mannans (at least one with a molecular weight <30,000 and at least one with a molecular weight between 100,000 and 500,000 or >750,000) at a concentration of between 0.5% and 5.0% wt/vol and at least one essential oil at a total concentration of between 0.5% and 5.0% vol/vol with the remainder being DI water.

An even more preferred embodiment of the topical application formulation is a combination of one glycosaminoglycan or mannan with a molecular weight <30,000 and one glycosaminoglycan or mannan with a molecular weight >750,000 (the total concentration of the polysaccharide component being between 0.5% and 3.0% wt/vol) and one or more essential oils with a total concentration of between 1.0% and 3.0% vol/vol, the remainder being DI water.

The most preferred embodiment of the topical application formulation is a combination of hyaluronic acid with a molecular weight <30,000 with hyaluronic acid with a molecular weight between 100,000 and 500,000 or >750,000 at a total hyaluronic acid concentration of between 0.5% and 3.0% wt/vol and an essential oil selected from the group comprising Rosemary Oil, Tea Tree Oil, Wintergreen Oil, Spearmint Oil, Peppermint Oil, Sweet Birch Oil, Eucalyptus Oil, Menthol and Camphor at a concentration of between 1.0% and 3.0% vol/vol with the remainder of the formulation being DI water. In order to provide the most effective, most acceptable (aroma and spreadability) and least expensive embodiment of this invention the formulation would contain 1.0% wt/vol hyaluronic acid (made up of equal volumes of low molecular weight hyaluronic acid and high molecular weight hyaluronic acid) combined with 2% wt/vol of a combination of Wintergreen Oil, Spearmint Oil, and/or Peppermint Oil with the remainder of the formulation being DI water.

Complex carbohydrates which we have specifically utilized in successful pharmaceutical compositions include heparin, hyaluronic acid, chondroitin sulfate, dermatan sulfate, keratan sulfate, and acemannan (active ingredient of Aloe Vera).

Essential oils which we have specifically utilized in successful pharmaceutical compositions include Tea Tree Oil, Rosemary Oil, Eucalyptus Oil, Wintergreen Oil, Sage Oil, Jojoba Oil, White Pine Oil, Camphor Oil, Cinnamon oil, Oil of Clove, Spearmint Oil, Peppermint Oil, EMU Oil, Sweet Birch Oil and Menthol.

The oral formulations of the immediate invention can include any of the complex carbohydrates, alone or in combinations and either with or without the presence of essential oil as an active ingredient, whereby the formulation is administered as a form selected from the group consisting of a liquid, an emulsion, a suspension, a cream, an ointment, a gel, a foam, a solid, a powder and a gum. It is contemplated that the liquid could be added to a drink or drink mix, to food, be a part of a soft drink, another type of carbonated drink, a supplement drink, used as a mouthwash or added to a mouthwash, as a toothpaste, as a gargle, as a spray, added to a vaporizor, as a liquid center of a gum or throat lozenge, or used in any other way so as to retain the effectiveness of the complex carbohydrate. A gel form could include a gel applied by mouth, to the gums, to the tongue, under the tongue, to the eyes, to the nose, to the vaginal area or vagina, or to the rectum. A foam could be added to wounds, to the mouth, to the gums, to the vagina or any other mucous membrane. A solid can be incorporated into food, treats such as candy or treats for animals, a chewing gum, a dissolvable gum, a lozenge, capsules, tablets, dissolvable tablets, suppositories and any other form that would not damage the effectiveness of the complex carbohydrates or the essential oils if used in the formulation. Other additives may be added to said oral formulations to improve taste and palatability or enhance the flavor. For instance, treats for horses may include sugar or a liquid or gel may be applied to a sugar cube. Treats for dogs may include liver or yeast flavoring.

The same formulations as mentioned for oral use can be used for mucosal delivery of the complex carbohydrates. The only limitation is that the formulation remain in contact with a mucosal surface for a period of at least a few seconds, preferably between 5 and 10 seconds.

Although the complex carbohydrates may be added to foods which are then baked, it is preferred to add the complex carbohydrates to the surface of the food after baking is complete. This retains the greatest activity.

It is contemplated that the complex carbohydrates of the present invention may be added to nutritional supplements to enhance their effectiveness. For instance, a mixture of complex carbohydrates and zinc, zinc gluconate, zinc gluconate glycine could be used for more effective treatment of sore throat and colds. A mixture of the complex carbohydrates of this invention and capsaisin may produce an even more effective treatment for joint pain and swelling. Addition of vitamins, minerals and other nutritional additives may produce enhancement of the nutritional activity by the complex carbohydrates.

The present invention has been found to be particularly effective in the treatment of any type of inflammation, pain and/or itching which is associated with the Adhesion cascade defined and described earlier. It is preferable for: treatment of muscle and joint inflammation and pain resulting from athletic injuries, treatment of inflammation and pain associated with arthritis and bursitis, and relief from pain often referred to as "tired feet", reduction of inflammation (edema) in extremities resulting from diabetes, reduction of inflammation and pain in addition to wound healing of decubitus ulcers resulting from poor circulation by diabetic patients or bedridden patients, treatment of inflammation and itching of skin resulting from allergic reactions such as poison ivy and insect bites/stings, treatment of inflammation and pain associated with tendonitis, treatment of inflammation and pain associated with muscle cramps, inhibition of bruising and inflammation post trauma or surgery if applied immediately, dissolution of bruises which have already formed, wound healing in superficial cuts and scrapes as well as wound healing after surgery to reduce scarring and adhesions, treatment of inflammatory skin conditions such as acne or psoriasis and treatment of dry skin, burns, or sunburn.

The most recent theories to explain heart attacks and stroke (Harvard Health Letter, December 1999, pgs 4 and 5, and SCIENCE vol:285, 23 Jul., 1999, pg 595-599) involves the eruption of unstable plaques which have been found to be infiltrated with T-cells and macrophages (leukocytes which cause inflammation) thus linking this disease syndrome to the Adhesion cascade. Therefore, it is expected that heart disease (heart attacks and stroke) can be prevented and treated with the complex carbohydrates of this invention. Therefore, it is expected that the complex carbohydrates of this invention can be used to prevent and/or treat heart disease. For example, is contemplated that hyaluronic acid, salts or derivatives thereof could be taken daily as a preventative for heart disease, and/or stroke. Amounts from 1 mg/day to 20 mg/day would be expected to prevent heart disease and stroke. This could be taken orally. Preferably, it would be taken mucosally. Alternately, a mixture of hyaluronic acid and chondroitin sulfate could be taken daily for prevention of heart disease and stroke. Again, the daily dose would be expected to be less than a total of 100 mg. Repeated low doses have been demonstrated to be between 0.0001 mg and 100 mg.

The most recent theory to explain the significant neurological degeneration that occurs in Alzheimer's Disease involves a substantial inflammatory component (SCIENCE, vol: 286, 17 Dec., 1999, pgs 2352-2355) which appears to be related to the Adhesion cascade. Therefore, it is expected that the complex carbohydrates of this invention can be used to prevent and/or treat Alzheimer's Disease. For example, it is contemplated that hyaluronic acid, salts or derivatives thereof could be taken daily as a preventative for Alzheimer's Disease. Amounts from 1 mg/day to 20 mg/day would be expected to prevent the degradation apparent in Alzheimer's Disease. This could be taken orally. Preferably, it would be taken mucosally. Alternately, a mixture of hyaluronic acid and chondroitin sulfate could be taken daily for prevention of Alzheimer's Disease. Again, the daily dose would be expected to be less than a total of 100 mg.

The most recent theory to explain the significant neurological degeneration that occurs after spinal cord injuries that leads to irreparable paralysis, is attack by the leukocytes rushing to the site of trauma (Adhesion cascade) to help repair the traumatized area, but instead, degrading the ends of the nerves in the spinal cord, fraying them which effectively inhibits their potential realignment and partial or complete repair. It is expected that paralysis resulting from spinal cord injuries could be prevented or treated effectively using the complex carbohydrates of this invention. In this case, since the patient may not be able to take an oral medication, the medication may be administered mucosally using suppositories (rectal or vaginal). The dose may need to be higher, in the range of 100 mg to 1,000 mg per day. It is also expected that drugs to assist repair of nerves would be administered concurrently.

The invention described herein is for use with any mammal including but not limited to humans, dogs, cats, horses, cattle swine, sheep, goats, etc.

The invention is further illustrated but is not intended to be limited by the following examples.

Example 1

High molecular weight (>750,000) cosmetic grade hyaluronic acid obtained from Meiji Seika Kaisha, Ltd, was dissolved in distilled/deionized water (DI) to a concentration of from 1.1 to 1.5% wt/vol. This solution was treated with high pH and high temperature to break down the molecular weight to <30,000. The latter treatment involved raising the pH. of the solution to 11.0 and mixing the hyaluronic acid at 37-60° C. for at least 4 hours. The viscosity of a 1% solution measured at 37° C. in a Cannon-Manning Viscometer dropped from >1000 c/s to <10 c/s as a result of this treatment. This hyaluronic acid was adjusted to 1.0% wt/vol by dilution in DI water. The 1.0% hyaluronic acid solution was aliquoted into 10 vials with 100 mL each. Various essential oils were added to each vial at a concentration of 2.0% vol/vol. The resulting suspensions were mixed at room temperature for 2-3 hours. The following essential oils were tested in this experiment: Rosemary Oil, Tea Tree Oil, Camphor Oil, Oil of Wintergreen, Eucalyptus Oil, Cinnamon Oil, Sage Oil, Jojoba Oil, Lemon Oil and Oil of Clove. All of the essential oils were obtained from Loranne Oils. All preparations were held at 4° C. for 14 days after which they were evaluated for their suspension characteristics and for their sterility. Suspension characteristics were evaluated visually while sterility was evaluated by placing a 0.1 mL sample onto a blood agar plate, incubating the plate at 37° C. for 7 days and observing the plates for the presence of colonies.

Tea Tree Oil, Eucalyptus Oil and Camphor Oil produced the best suspensions. These suspensions remained stable while the others separated out with the oil either dropping out or rising to the top of the hyaluronic acid solution.

Each suspension was remixed and aliquoted into 10 mL amounts in 25 mL vials. Five patients with localized chronic pain complaints were given one vial of each preparation over a period of 2 months. After using the first preparation, they were interviewed about effectiveness, safety (development of rashes or other adverse reactions), spreadability/feel and odor. Effectiveness was evaluated on a scale of 1 to 5 with 5 being the most effective (most relief of their condition). Safety was evaluated by noting any adverse effects. Spreadability was evaluated on a 1 to 3 scale with 3 being best. Odor was evaluated on a scale of 1 to 3. Pleasing was defined as 3 while unpleasing was given a value of 0. At this point, they were given the second preparation to evaluate. The third through 11th preparations were evaluated in the same manner.

The 11th preparation contained hyaluronic acid without essential oils. Results are summarized in Table 1.

Interviews with all patients were positive in that all patients reported immediate relief within 5 minutes of applying the topical preparations. Two reported relief within 30 seconds of treatment. None of the patients reported that the hyaluronic acid alone was effective. None of the patients noticed untoward reactions. Spreadability was not ideal and most of the patients complained that the suspension was too thin and difficult to apply. However, they liked the fact that the preparations were not oily. The odors of the preparations were generally pleasing. Only Tea Tree Oil and Sage Oil produced "unpleasing" comments. All patients commented that even though the preparation had an odor at application, there was no residual odor noted within a few minutes after application.

The medical complaints of the patients being treated in this study included:
1. Chronic knee pain/swelling post knee surgery for chondromalacia
2. Chronic knee pain/swelling as a result of torn cartilage
3. Chronic pain/swelling in first and second finger of right hand diagnosed as arthritis
4. Chronic foot pain (undiagnosed)
5. Chronic pain in left thumb/wrist post reconstructive surgery

TABLE 1

EVALUATION OF COMBINATIONS OF ESSENTIAL OILS WITH LOW MOLECULAR WEIGHT HYALURONIC ACID

| Oil | Effectiveness | Safety | Spreadability | Odor |
|---|---|---|---|---|
| Rosemary | 5 | No Rxs | 2 | 3 |
| Tea Tree | 5 | No Rxs | 2 | 1.7 |
| Camphor | 4 | No Rxs | 1 | 3 |
| Wintergreen | 5 | No Rxs | 2 | 3 |
| Eucalyptus | 5 | No Rxs | 1.7 | 3 |
| Cinnamon | 4 | No Rxs | 2 | 3 |
| Sage | 4 | No Rxs | 1.7 | 1 |
| Jojoba | 4 | No Rxs | 1.7 | 1.7 |
| Lemon | 3 | No Rxs | 1.7 | 2 |
| Clove | 4 | No Rxs | 1.7 | 3 |
| None * | 0 | No Rxs | 2 | 3 |

* Control—Contains only hyaluronic acid with no essential oils
No Rxs = No reactions observed by patients
The Effectiveness, Spreadability and odor scores are averages of the 5 responses.

Example 2

High molecular weight (>750,000) cosmetic grade hyaluronic acid was obtained from Meiji Sieka Kaisha, Ltd. It was dissolved in distilled/deionized water (DI) to a concentration of 1.0% wt/vol. The viscosity of this solution at 37° C. was >1000 c/s and the molecular weight was >750,000. The 1.0% hyaluronic acid solution was aliquoted into 10 vials with 100 mL each. Various essential oils were added to each vial at a concentration of 2.0% vol/vol. The resulting suspensions were mixed at room temperature for 2-3 hours. The following essential oils obtained from Loranne Oils were tested in this experiment: Rosemary Oil, Tea Tree Oil, Camphor Oil, Oil of Wintergreen, Eucalyptus Oil, Cinnamon Oil, Sage Oil, Jojoba Oil, Lemon Oil and Oil of Clove. All preparations were held at 4° C. for 7 days after which they were evaluated for their suspension characteristics and for sterility according to procedures described in EXAMPLE 1. All oils remained in suspension due to the viscosity of the hyaluronic acid. All of the preparations appeared sterile. Each suspension was remixed and aliquoted into 10 mL amounts in 25 mL vials. The same five patients with localized chronic pain complaints who evaluated the preparations in EXAMPLE 1 evaluated these preparations. At the same time that they were given the vials in Example 1, they were given the corresponding vial from this example. They were instructed to compare the two preparations with the same essential oil (denoted by numbers). After using the first preparation, they were interviewed about effectiveness, safety (development of rashes or other adverse reactions), feel (spreadability) and odor. Effectiveness was evaluated on a scale of 1 to 5 with 5 being the most effective (most relief of condition). Safety was evaluated by noting any adverse effect. Spreadability was evaluated on a 1 to 3 scale with 3 being best. Odor was evaluated on a scale of 1 to 3. Pleasing was defined as 3 while unpleasing was defined as 0. At this point, they were given the second preparation to evaluate. The third through 11th preparations were evaluated in the same manner. Results are summarized in Table 2. All numbers shown in this table are averages of the responses.

Patients indicated that although these preparations were as effective as the preparations in EXAMPLE 1, it took from 45 to 60 minutes for the effect to be significant. However, they indicated that the effect lasted for 4-8 hours. The effectiveness of preparations in EXAMPLE 1 seemed to last only 1-3 hours. All patients liked the spreadability of the preparations in EXAMPLE 2. All except the Camphor Oil spread smoothly and left the skin feeling soft. The Camphor Oil seemed to absorb rapidly leaving the skin feeling dry. Again, no adverse reactions were noted.

The complaints of the patients in this study included:
1. Chronic knee pain/swelling post knee surgery for chondromalacia
2. Chronic knee pain/swelling as a result of torn cartilage
3. Chronic pain/swelling in first and second finger of right hand diagnosed as arthritis
4. Chronic foot pain (undiagnosed)
5. Chronic pain in left thumb/wrist post reconstructive surgery

TABLE 2

EVALUATION OF A COMBINATION OF ESSENTIAL OILS WITH HIGH MOLECULAR WEIGHT HYALURONIC ACID

| Oil | Effectiveness | Safety | Spreadability | Odor |
|---|---|---|---|---|
| Rosemary | 4 | No Rxs | 3 | 3 |
| Tea Tree V | 4 | No Rxs | 3 | 1.7 |
| Camphor | 3 | No Rxs | 2 | 3 |
| Wintergreen | 4 | No Rxs | 3 | 3 |
| Eucalyptus | 4 | No Rxs | 3 | 3 |
| Cinnamon | 2 | No Rxs | 3 | 3 |
| Sage | 2 | No Rxs | 3 | 1 |
| Jojoba | 3 | No Rxs | 3 | 1.7 |
| Lemon | 2 | No Rxs | 3 | 2 |
| Clove | 2 | No Rxs | 3 | 3 |
| None * | 0 | No Rxs | 3 | 3 |

*Control—Contains only hyaluronic acid with no essential oils
No Rxs = No Reactions
Effectiveness, Spreadability and odor scores are averages of the 5 responses.

Example 3

A 1.0% wt/vol solution of dermatan sulfate (chondroitin sulfate B obtained from SIGMA Chemical Company) was prepared using DI water. The viscosity of this preparation was <10 c/s. The molecular weight was 15,000. This preparation was mixed 1:1 with the 1.0% wt/vol high molecular weight hyaluronic acid solution described in EXAMPLE 2. Five aliquots of 30 mL each were dispensed into vials. To the first aliquot was added 2.0% vol/vol Rosemary Oil. To vials 2-4 was added either Eucalyptus Oil, Wintergreen Oil or Tea Tree Oil (all obtained from Loranne Oils). No essential oils were added to the fifth vial. All preparations were held at 4° C. for 7 days after which they were evaluated for their suspension characteristics. All oils remained in suspension due to the viscosity of the hyaluronic acid. Each suspension was remixed and aliquoted into 10 mL amounts in 25 mL vials. Three patients with chronic pain/swelling complaints were given one vial of each preparation to evaluate. They were asked to compare effectiveness, safety, spreadability and odor. The same numerical scales for evaluation of these parameters were used as is noted in EXAMPLES 1 and 2. Results are listed in Table 3.

The general response was that all preparations provided relief within 5 minutes and such relief lasted up to 6 hours. Also, spreadability was totally acceptable to all patients. It appears that this combination is more effective than the lower molecular weight preparation described in EXAMPLE 1 in that it provides both quicker and longer-lasting relief from pain. The control preparations containing only the essential oils did not provide relief and were not acceptable for spreadability. The control which contained only the dermatan sulfate and hyaluronic acid components ("NONE") was not effective.

The complaints of these patients included:
1. Chronic pain in left leg resulting from diagnosed osteoarthritis of the left hip
2. Chronic neck pain resulting from diagnosed stenosis and bone spur formation requiring surgery
3. Chronic tired feet (patient on feet on concrete floors all day)

TABLE 3

COMPARISON OF MIXTURES CONTAINING DERMATAN SULFATE, HIGH MOLECULAR WEIGHT HYALURONIC ACID AND VARIOUS ESSENTIAL OILS

| Oil | Effectiveness | Safety | Spreadability | Odor |
|---|---|---|---|---|
| Rosemary | 5 | No Rxs | 3 | 3 |
| Eucalyptus | 5 | No Rxs | 3 | 3 |
| Wintergreen | 5 | No Rxs | 3 | 3 |
| Tea Tree | 5 | No Rxs | 3 | 1.7 |
| None * | 0 | No Rxs | 3 | 3 |
| Rosemary only ** | 0 | No Rxs | 0 | 3 |
| Wintergreen Oil ** | 0 | No Rxs | 0 | 3 |
| Tea Tree Oil ** | 0 | No Rxs | 0 | 1.7 |

* = Control—Contains only dermatan sulfate and hyaluronic acid with no essential oils
** = Contains only the listed essential oil and no hyaluronic acid
No Rxs = No reactions
Numerical values for effectiveness, spreadability and odor are averages of the 3 responses.

Example 4

In order to determine whether a combination of a high and low molecular weight mixture of a salt of hyaluronic acid would produce results similar to those described in EXAMPLE 3, the following experiment was conducted. High molecular weight (>750,000) cosmetic grade hyaluronic acid (obtained from Meiji Seika Kaisha, Ltd.) was prepared as in EXAMPLE 2. The concentration of this solution was adjusted to 1.0% wt/vol. The viscosity of this solution at 37° C. was >1000 c/s and the molecular weight was >750,000. Low molecular weight cosmetic grade hyaluronic acid (from the same source) was prepared as described in EXAMPLE 1. The resulting hyaluronic acid solution was adjusted to 1.0% wt/vol by dilution in DI water. Equal volumes of high molecular weight and low molecular weight hyaluronic acid solutions were mixed and aliquoted into 50 mL portions. To the first aliquot was added 2.0% vol/vol Rosemary Oil. To vials 2-4 were added either Eucalyptus Oil, Oil of Wintergreen or Tea Tree Oil, each at 2.0% vol/vol. No essential oils were added to the fifth vial. All preparations were held at 4° C. for 7 days after which they were evaluated for their suspension characteristics. All oils remained in suspension due to the viscosity of the hyaluronic acid solution. Each suspension was remixed and aliquoted into 10 mL amounts. Three patients with chronic pain/swelling complaints were given one vial of each preparation to evaluate. They were asked to compare effectiveness, safety, spreadability and odor. The same numerical scales for evaluation were used as noted in EXAMPLES 1-3. Again, the results are listed as averages of the three responses. Results are listed in TABLE 4.

The general response was that all preparations provided relief within 5 minutes and such relief lasted up to 6 hours. Also, spreadability was totally acceptable to all patients. It appears that this combination is as effective as a mixture of low molecular weight dermatan sulfate and high molecular weight hyaluronic acid in that it provides quicker and longer relief from pain. The control preparations containing only the hyaluronic acid (NONE *) did not provide relief. The control preparations containing only essential oils (Tea Tree Oil or Wintergreen Oil) did not provide relief.

Patients generally commented that the preparations were not oily upon application, a quality that all appreciated. Also, all patients commented that although there is some odor upon topical application, there is no residual odor—no odor could be detected by a few minutes after application.

The complaints of these patients included:
1. Chronic pain in left leg resulting from diagnosed osteoarthritis of the left hip
2. Chronic neck pain resulting from diagnosed stenosis and bone spur formation requiring surgery
3. Chronic tired feet (patient on feet on concrete floors all day)

TABLE 4

EVALUATION OF A MIXTURE OF HIGH AND LOW MOLECULAR WEIGHT HYALURONIC ACIDS

| Oil | Effectiveness | Safety | Spreadability | Odor |
|---|---|---|---|---|
| Rosemary | 5 | No Rxs | 3 | 3 |
| Eucalyptus | 5 | No Rxs | 3 | 3 |
| Wintergreen | 5 | No Rxs | 3 | 3 |
| Tea Tree | 5 | No Rxs | 3 | 1.7 |
| None * | 0 | No Rxs | 3 | 3 |
| Tea Tree ** | 0 | No Rxs | 0 | 1 |
| Wintergreen ** | 0 | No Rxs | 0 | 3 |

* Control—Contains only hyaluronic acids and no essential oils
** Contains only the essential oil listed but no hyaluronic acid
No Rxs = No reactions
Numerical scores for effectiveness, spreadability and odor are averages of the three responses Example 5

Heparin sulfate has long been known as an anticoagulant when administered intramuscularly, intravenously or subcutaneously. However, to our knowledge it has never been used topically. Since dermatan sulfate and hyaluronic acid are topically effective when mixed with essential oils, it was of interest to determine whether heparin sulfate could also be topically effective. Heparin sulfate was purchased from Rhone Poulenc Rorer in liquid form at a concentration of 30 mg/0.3 mL. This preparation was diluted to 30 mg/mL (3.0% wt/vol) with DI water and aliquoted in 1.0 mL amounts. One percent vol/vol Rosemary Oil was added to one aliquot, 2.0% vol/vol Rosemary Oil was added to a second aliquot and 2.0% vol/vol Wintergreen Oil was added to a third aliquot. One aliquot contained no essential oils and was used as a control (Hep Only in TABLE 5). All essential oils were obtained from Loranne Oils.

These formulations were compared in their ability to treat various medical complaints. Patients were given one of each preparation and requested to evaluate the effectiveness of the preparations. Effectiveness was evaluated on the basis of good (G), fair (F) or poor (P). After use of the preparations for a period of at least one month, patients were interviewed as to their satisfaction with the products. Results of these interviews are presented in TABLE 5.

TABLE 5 indicates that Heparin sulfate mixed with essential oils appears to work effectively when applied topically to treat bruising, torn muscles, sprains and tendonitis. According to the interviews, the 1.0% solution may have had a slightly shorter effect with some of the more painful medical complaints. Heparin sulfate alone (without essential oils) had no effect when applied topically.

TABLE 5

ACCEPTABILITY OF HEPARIN/ESSENTIAL OIL MIXTURES

| Patient Complaint | Effectiveness | | | | Comments |
|---|---|---|---|---|---|
| | 1% R | 2% R | 2% TT | Hep Only | |
| Extensive bruise | G | | | | 4cm × 8cm bruise resolved much faster than normal |
| Torn muscle in rt. thigh | G | | | | Noticed short-term improvement, multiple applications necessary for resolution |
| Ankle sprain with bruising and swelling | | G | | | Bruise resolved in 3 days, ankle supported full weight in 2 days |
| Tendonitis— rt. Elbow | | G | | | Required 3-4 treatments/day for 3 months for complete resolution |
| Torn muscle in left calf | | G | | | Patient supported full weight in 2 days |
| Chronic cramping of Foot | | | G | | Cramps resolved within 1 minute and did not return for 4 hours |
| Acute muscle cramp-rt. calf | | | G | | Cramp was relieved within 30 seconds |
| Chronic knee pain: chondromalacia | | | | P | No Relief was noted |
| Torn muscle in rt. thigh | | | | P | No effect was noted |

1% R = A mixture containing 3% heparin plus 1% Rosemary Oil
2% R = A mixture containing 3% heparin plus 2% Rosemary Oil
2% TT = A mixture containing 3% heparin plus 2% Tea Tree Oil
Hep only = Control—A mixture containing 3% heparin without an essential oil Example 6

In order to determine the effect of an extract of the Aloe Vera plant, Aloe Vera gel concentrate which has acemannan as one of its active ingredients, was obtained from Lily of the Desert. Thirty milliliter aliquots of this Aloe Vera gel concentrate (99.0% pure) were placed into vials. To one aliquot was added 1.0% vol/vol Wintergreen Oil, to a second aliquot was added 2.0% vol/vol Wintergreen oil, to a third aliquot was added 2.0% vol/vol Tea Tree Oil, to a fourth aliquot was added 2.0% vol/vol Rosemary Oil and to a 5th aliquot was added 2.0% vol/vol Eucalyptus Oil. One aliquot contained no oil and was used as a control (NONE * in TABLE 6). All aliquots were held at 4° C. for 7 days after which they were evaluated for their suspension characteristics. All oils remained in suspension due to the viscosity of the Aloe Vera gel concentrate. Each suspension was remixed and aliquoted into 10 mL amounts. Three patients with chronic problems resulting in pain and swelling were given one vial of each preparation to evaluate. They were asked to compare effectiveness, safety, spreadability and odor. The same numerical scales for evaluation of these parameters were used as described previously in EXAMPLE 1. Results are listed in TABLE 6. All numerical values are averages of the responses of the 3 patients.

TABLE 6

EVALUATION OF A MIXTURE OF ALOE VERA AND ESSENTIAL OILS

| Preparation (Oil) | Effectiveness | Safety | Spreadability | Odor |
|---|---|---|---|---|
| Tea Tree | 4 | No Rxs | 1.7 | 1 |
| Wintergreen 1% | 3 | No Rxs | 1.7 | 3 |
| Wintergreen 2% | 4 | No Rxs | 1.7 | 3 |
| Rosemary | 4 | No Rxs | 1.7 | 3 |
| Eucalyptus | 4 | No Rxs | 1.7 | 3 |
| None * | 0 | No Rxs | 1.7 | 3 |

Control—Contains Aloe Vera Only—no essential oil added
No Rxs = No reactions
Numerical values for effectiveness, spreadability and odor are averages of the 3 responses The complaints of the patients in this study included:
1. Acute tendonitis of the right elbow
2. Torn muscle in the right calf
3. Chronic knee pain/swelling as a result of torn cartilage Patients indicated that all preparations produced equivalent results reducing pain and swelling. The positive effects were noted within 5 minutes and lasted for 2-4 hours. Spreadability was acceptable to all patients. None of the preparations produced adverse reactions. The control preparation containing only the Aloe Vera gel concentrate was ineffective.

Example 7

An 83 year old male suffering from terminal colon cancer was bedridden for 5 months. The family of caregivers was informed that bedsores would be a major problem for the patient and that they should notify the hospice nurses when such condition began to develop. Hospice nurses checked the patient two times per week during the first three months of the patient's incapacitation. Later, the Hospice nurses visited three days per week checking on the patient's well-being. The patient was given a combination of low and high molecular weight hyaluronic acids formulated with Oil of Wintergreen (prepared as in EXAMPLE 4) as a preventative before any indication of bedsores was noted. Areas of the body which appeared reddened from pressure (e.g. buttocks, rib cage on back and shoulder blades) were massaged with the formulation once or twice per day (depending on the patient's tolerance to movement). The patient never developed bedsores. It should be noted that the patient was not routinely turned as suggested by the nurses because this procedure was too painful. Therefore, the development of bedsores was expected. The Hospice nurses were amazed and commented repeatedly about the use of the formulation to prevent bedsores.

Example 8

A 93 year old male who was bedridden as a result of Alzheimer's disease for 1.5 years was treated with a formulation containing 2.0% Rosemary Oil (Rosemary Oil was obtained from Loranne Oils) and 1.0% dermatan sulfate (chondroitan sulfate B obtained from SIGMA Chemical Company) for one year while at home. The treatment included massaging the buttocks, back and shoulders with the formulation once or twice per day. During this period of treatment the patient developed no bedsores. After transfer to a nursing home which did not allow the use of the formulation, the patient developed bedsores within 2 weeks. He had continuing problems with such ulcers until his death.

Example 9

A 45 year old female who was extremely sensitive to poison ivy was given a formulation containing a combination of 1.0% wt/vol high molecular weight hyaluronic acid (400,000-500,000) and 2.0% Rosemary Oil to use on an active case of poison ivy. The formulation was prepared by using hyaluronic acid obtained from LIPO CHEMICALS, INC. and Rosemary Oil obtained from Loranne Oils. Other topical treatments such as Benadryl, Dermarest, Hydrocortisone 0.5%, etc. provided only temporary relief and the dermatitis with weeping pustules remained active. The individual was so sensitive that poison ivy desensitization injections were not tolerated. This individual reported that topical use of the hyaluronic acid combined with Rosemary Oil applied directly onto the weeping pustules caused an initial stinging but that relief from itching occurred "within minutes". The relief was temporary as with cortisone creams. However, she reported that the pustules dried up and resolved "within a few days". In the past this individual noted that the poison ivy pustules would remain up to 6 weeks.

Example 10

The same 45 year old female from EXAMPLE 9 was exposed to poison ivy again while she was using a weed-eater to trim around the house. This time, after the pustules appeared all over the legs, she was given a formulation which contained 0.01% high molecular weight hyaluronate (Lifecore Biomedical, Inc.) mixed with 99.99% Peppermint Oil. She reported that this mixture provided significantly longer relief from itching (approximately 8 hours) but that the oils were so volatile that the preparation bothered her eyes. The preparation was substituted for one which contained a mixture of high and low molecular weight sodium hyaluronate (as prepared in EXAMPLE 4 mixed with 1% Wintergreen Oil, 1% Spearmint Oil and 0.5% Peppermint Oil. This provided the same relief from itching for 6-8 hours and did not bother her eyes. She reported that the preparation felt cool after application to the pustules and at the point that the cooling effect was noted, the itching disappeared. Therefore, for treatment of conditions involving itching, it is desirable to include an essential oil that provides a cooling effect.

Example 11

A 57 year old bedridden diabetic patient suffering from edema of the lower extremities complicated by chronic problems with decubitus ulcers obtained one of the formulations of this invention to try. This patient was given a formulation containing a combination of 1.0% wt/vol high molecular weight hyaluronic acid and 1.0% wt/vol dermatan sulfate (in a 1:1 ratio) formulated with 2.0% vol/vol Oil of Wintergreen. The hyaluronic acid for this formulation was obtained from Genzyme, Inc., the Dermatan sulfate was obtained from SIGMA Chemical Company and the essential oils were obtained from Loranne Oils. The preparation was applied three times per day onto the decubitus ulcers and generally onto the lower extremities. The patient reported that within one week the edema was resolved and the ulcers were healing. Within one month he was out of bed and back to work. This was a significant improvement since he had not been able to work for 6 months. This patient has continued to use this formulation over a two year time period with no adverse side effects and no return of his condition.

Example 12

A 27 year old female with chronic acne since puberty was given a preparation containing 1.0% wt/vol hyaluronic acid in combination with 1.0% vol/vol Wintergreen Oil. The molecular weight of the hyaluronic acid used to formulate this preparation was obtained from Genzyme, Inc. and had a molecular weight of between 550,000 and 650,000. The Wintergreen Oil was obtained from Lorann Oils. This individual applied the preparation twice per day (morning and evening). After 2 weeks she reported a significant improvement in healing of the active eruptions and also reported smoothing of the skin. After one month she reported that her face was free of eruptions and that the skin felt smoother than ever before. This individual has continued using the preparation for 2 years without return of her acne problem and without development of any adverse reactions.

Example 13

A preparation containing 99% Aloe Vera gel concentrate (obtained as 99% pure from Lily of the Desert) to which was added 2.0% vol/vol Wintergreen Oil (obtained from Lorann Oils) and 0.2% vol/vol high molecular weight (>1,000,000) hyaluronic acid (obtained from Lifecore Biomedical, Inc.) was given to three individuals suffering from knee problems involving pain and swelling. The first patient had been diagnosed with chondromalacia, the second patient with torn cartilage and the third patient had been diagnosed with osteoarthritis. Each patient used the preparation for a period of one month after which they were interviewed about the effectiveness, safety and spreadability of the formulation. The responses are summarized in TABLE 7.

Each of the patients commented that they were impressed that the preparation was not oily and that there was no lingering odor after topical application.

TABLE 7

SUMMARY OF RESULTS ON USE OF A COMBINATION OF ALOE VERA, OIL WINTERGREEN AND HYALURONIC ACID TO TREAT PAIN AND ASSOCIATED WITH KNEE PROBLEMS

| Diagnosis | Effectiveness | Safety | Spreadability |
|---|---|---|---|
| Chondromalacia | Excellent at a use rate of 3 applications/day | No Reactions | Too thin |
| Torn cartilage | Good—relief for 1-2 hours after treatment | No Reactions | Would prefer something thicker |
| Osteoarthritis | Excellent at a use rate of 2 applications/day | No Reactions | Excellent results |

Example 14

A preparation containing a 1:1 ratio of 1.0% wt/vol low molecular weight hyaluronic acid (prepared from a liquid 1.0% solution obtained from Lifecore Biomedical and treated according to the description in EXAMPLE 1 to produce a molecular weight of <30,000) and 1.0% wt/vol high molecular weight hyaluronic acid (obtained from Lifecore Biomedical and containing a molecular weight >500,000) and 2.0% vol/vol Rosemary Oil (obtained from Loranne Oils) was provided to two patients with diagnosed psoriasis. The patients were instructed to use the preparation for one month and report their results during an interview. The interviews indicated that both patients noted immediate improvement in the skin texture and a reduction in pain. This occurred within two days of initiating the treatment. The lesions were beginning to resolve by the one month interview. These individuals have been followed for 6 months and report continued improvement.

Example 15

A 42 year female indoor soccer player who played goalie and suffered from repeated rug (indoor turf) burns on the knees was given a preparation of 1.0% wt/vol dermatan sulfate combined with 2.0% vol/vol wintergreen oil. This preparation was produced by adding 1.0 g of chondroitin sulfate B (obtained from SIGMA Chemical Company) to 100 mL of DI water and mixing until dissolved. To this solution was added the essential oil. This individual applied the solution immediately after the injury occurred and twice more at 4 hours and 12 hours after the injury. The patient commented that the solution caused great stinging and pain upon application. However, the rug burn was almost healed within 72 hours. This was compared to similar burns which she had sustained in past months which took up to 3 weeks to heal because they kept weeping. Since the patient was concerned about the stinging and pain upon application, a second formulation was prepared for her to try on the next rug burn. This second formulation contained the same chondroitin sulfate B mixed with 2.0% vol/vol Tea Tree Oil. Several weeks later the individual suffered another rug burn that was treated with the Tea Tree Oil preparation. The patient commented that this preparation was much better, causing only minimal discomfort upon application. The healing process again required only 96 hours instead of weeks. General comments were that the preparation caused the wound to produce a scab within a few hours and that this scab became dry and fell off within a few days. Additionally, the patient liked the fact that the solution was not greasy nor did it leave a lingering odor.

Example 16

A 48 year old female suffered from chronic eczema—scaly and red areas on her neck and arms. She had tried all types of treatments, including cortisone with no effect. She was given a preparation containing a mixture of low and high molecular weight sodium hyaluronate (prepared as in EXAMPLE 4) mixed with 1% Wintergreen Oil, 1% Spearmint Oil, and 0.5% Peppermint Oil. She applied it for one week. She noted that the eczema disappeared after the $3^{rd}$ day of treatment but continued treatment to make sure that it would not return. She has not treated the area for 2 months and has noted no return of signs of eczema.

Example 17

A 45 year old female softball player tore the quadriceps muscles of both the right and left thighs. Within 4 hours of the injury, this individual was given a preparation containing 1.0% wt/vol high molecular weight (>750,000) hyaluronic acid (Genzyme, Inc.) mixed with 2.0% vol/vol Tea Tree Oil and 2.0% Wintergreen Oil (both oils obtained from Lorann Oils). The individual was also given FLEXALL 454 to use as a control. She used no ice or heat treatments after the injury. To the right quadriceps she applied the hyaluronic acid/Tea Tree Oil/Wintergreen Oil (preparation of this invention). To the left quadriceps she applied the FLEXALL 454 (Control). Three applications of each preparation were made during the late afternoon and evening on the day of the injury. By the time the first applications were made, this individual could not walk and both quadriceps were extremely painful. By the third application, the individual noted that the right quadriceps felt less painful. When the individual awoke the morning after the injury she immediately applied both preparations to the respective quadriceps and stayed in bed for one hour longer. After the one hour time period she decided to try to walk. The right quadriceps was reportedly much better and she was able to support weight on this leg (the quadriceps receiving the treatment of this invention). The left quadriceps was still as painful as it was the day before (no relief was noted). On the second day, 4 more applications of each preparation were made to the respective quadriceps. By the end of the day, the right quadriceps was "significantly improved" whereas the left quadriceps was more painful than the day before. On the morning of the third day post injury, after the morning application of the respective preparations, the individual reported that the right quadriceps felt "essentially normal" but the left quadriceps was still unchanged and very painful. At this time, the individual began using the treatment of this invention on the left quadriceps instead of the FLEXALL 454. Within 24 hours she reported that she could walk on the left leg and by 48 hours after switching treatments she was able to walk normally. In this direct comparison the hyaluronic acid/Tea Tree Oil/Wintergreen Oil formulation of this invention relieved the pain and inflammation of the muscle tear within 72 hours and, obviously stimulated healing, whereas an over-the-counter product suggested for this purpose was ineffective.

Example 18

A 53 year old male burned his right forearm while working on the muffler of his motorcycle. The burned area was 8 cm×12 cm and was beginning to redden and raise at the time that a formulation of this invention was applied to the area. This individual had received a formulation prepared by combining 1.0% wt/vol high molecular weight hyaluronic acid (obtained from Lifecore Biomedicals, Inc. and demonstrating a molecular weight >500,000) with 1.0% chondroitin sulfate B (obtained from SIGMA) and adding 2.0% Rosemary Oil, approximately 8 months before this accident in order to treat a severe sunburn. He still had some of the formulation of this invention left and applied it immediately to the burn. He reported that it immediately felt cool and that within 5 minutes the severe pain had dissipated. The burn did not blister as he had expected. Within 24 hours all that was noticeable was a reddened area of skin which was not painful and not granulated. Within 5 days there was no indication that a burn had occurred.

Example 19

A 52 year old male suffered a severe sunburn while boating. He tried several sunburn lotions to relieve the pain and redness but none of these preparations provided relief. He was feverish (temperature 101° F.). He was given a preparation containing 1.0% wt/vol high molecular weight hyaluronic acid (Lifecore Biomedical), 1.0% wt/vol low molecular weight hyaluronic acid (same preparation as described in EXAMPLE 1), 2.0% vol/vol Tea Tree Oil and 2.0% vol/vol Wintergreen Oil in an aqueous base. This was applied to his back, shoulders and arms. Within 5 minutes he commented that the burning sensation was gone. One hour after the application this patient's body temperature was back to normal. He continued to apply the preparation for 24 hours after which he discontinued treatment because he felt normal. The sunburned areas never peeled nor caused additional problems.

Example 20

A 76 year old male developed a severe case of poison ivy which had already spread over both legs from the ankles to the upper thighs as well as to the back prior to treatment. He reported that the itching was intolerable during the night and that he inadvertently scratched his legs so much that they were raw and bleeding. He had tried commercial products including Cortaid, Benzacaine and Caladryl with no significant relief. All provided only a few minutes of relief or none at all. His physician had suggested cortisone injections. Instead of subjecting himself to cortisone injections, he decided to try a preparation comprising an essential oil and a complex carbohydrate. The first formulation that was prepared for this patient consisted of 0.01% vol/vol hyaluronic acid mixed with 1% vol/vol Wintergreen Oil and 98.99% vol/vol Peppermint Oil. The patient was instructed to apply the preparation onto all of the areas covered by poison ivy. After the first application, the patient reported that the treated area burned for about 15 minutes and then felt cool. After the first 15 minutes the itching was relieved for approximately 6 hours. He complained of the burning sensation. A new formulation was provided. This latter formulation contained no Wintergreen Oil. Therefore, it contained 0.01% vol/vol hyaluronic acid and 99.99% vol/vol Peppermint Oil. This preparation was reported to burn much less after application. The patient continued treatment, reporting that the itching was relieved for 8-10 hours after application. Additionally, the poison ivy quit spreading and healed very quickly. In fact, this patient was able to discontinue treatment 5 days after starting his first treatment. The patient reports excellent results in treatment of poison ivy. It is believed that the essential oil which provides the best effect against, itching (anti-pruritic) is one which provides a cooling sensation on the skin. Therefore, the Peppermint Oil and other similar cooling oils provide longer relief than Wintergreen Oil or Menthol which produce a hot sensation and the Peppermint Oil does not produce a burning sensation on the skin.

Example 21

The following example describes use of a composition comprising a 1% wt/vol low molecular weight (<300,000) sodium hyaluronate plus 2% Wintergreen oil. Three individuals were stung by yellow jackets or bees. The composition was applied to the area over and around the sting within about 15 minutes. The following table indicates the effectiveness of the composition. Each patient reported immediate relief of the pain upon application of the composition. Additionally, each patient reported a lack of swelling post treatment. Only one treatment was used in each case. Even a person who was normally allergic to stings reported no allergic side effects.

Example 22

A 55 year old female who was known to be very susceptible to reaction to poison ivy was provided a mucosal composition comprising a mixture of high and low molecular weight sodium hyaluronate (as described in EXAMPLE 4) with no oils added. She had been helping other with cutting wood and noticed that there was a poison ivy vine wound around one of the logs that she was carrying in her bare arms. After completing the wood-cutting, she began taking the hyaluronate preparation orally. She took 10 mg in the morning and 10 mg at night for a period of 5 days. Twenty four hours after her exposure she noticed 2 "pinpoint" pustules on her arms. These never spread and disappeared by the third day. It is apparent by this example that oral glycosaminoglycans can prevent the development of an allergic reaction such as a rash caused by poison ivy.

Example 23

An 18 year old female suffered from chronic fibromyalgia of the face and neck. This condition had existed for approximately 5 years. There was nothing that provided relief for her condition. She was given a formulation containing a mixture of high and low molecular weight sodium hyaluronate (prepared according to EXAMPLE 4) to use orally. She took 10 mg two times per day (AM and PM). She reported that after only 1 day, her symptoms disappeared. She has continued to take the same dose for 6 months and has reported no return of her fibromyalgia. Therefore, a condition that has historically remained untreatable, is treatable with the compositions of the present invention.

Example 24

A 9 year old male suffering from severe Attention Deficit Hyperactivity Disorder (ADHD) complicated by Turret's Syndrome, who was being treated by diet control with little success, was given a sample of the mixture used in EXAMPLE 23. He took 10 mg in the morning and 10 mg in the evening, using the solution as a mouthwash (holding it in his mouth for about 10 to 20 seconds and then swallowing). His parents kept very strict records of his activity and noted that his ADHD was fully controlled and he suffered no "tics" while taking the sodium hyaluronate. The one day that he forgot to take his morning dose he had a recurrence of his "tics" and became almost uncontrollable. However, within 15 minutes of his receiving the missing dose, he became calm and returned to normal. This boy has remained totally under control for 2 months. This has never been observed before, even when he was taking Ridlin. He had discontinued taking Ridlin 1.5 year before because of problems with side effects. The sodium hyaluronate has provided no adverse reactions or side effects.

Example 25

A 60 year old male and 55 year old female (brother and sister) who routinely suffered severe sunburns the first few times that they were in the sun each summer, had been taking oral sodium hyaluronate gel for treatment of pain associated with a cervical disc stenosis (male) and chronic osteoarthritis of both knees (female). Pain from the conditions being treated was totally controlled by taking 5-10 mg twice per day. The sodium hyaluronate gel was prepared by adding sodium hyaluronate (Collaborative Laboratories, Inc) to a 1% concentration. This preparation had a molecular weight of >1,000,000. The gel was being applied directly on the tongue by dropper bottle. Both went on vacation together and spent most of 5 days in the bright sun in a boat. They did not use a sun blocker. Each previous year both had suffered severe discomfort from sunburn after the first day's exposure. This time, at the end of the 5 days, both noted that they were not sunburned, had suffered no discomfort and were developing a nice tan. It is believed that the preparation of this invention prevented sunburn, allowing tanning to occur.

Example 26

A 60 year old male suffering from colon cancer had been unable to tolerate his colostomy and demanded that his surgeon reconnect his intestines. He refused chemotherapy but requested a preparation prepared according to this invention. He was given a formulation of sodium hyaluronate (Collaborative Laboratories, Inc) which was prepared with a mixture of molecular weights of hyaluronate (as in EXAMPLE 4). When he began taking the hyaluronate preparation, his CEA was 70.1. He has taken the hyaluronate at a dose of 10 mg three times per day mucosally and after 6 months of treatment his CEA has dropped to 4.1. He has taken no other treatments. This patient had also suffered from polymyositis for 15 years. For this he was taking 50 mg of Prednisone daily without much relief. He reported that after 1 week of taking the hyaluronate preparation he felt complete relief from the pain caused by his polymyositis. After 6 months he has been able to reduce his Prednisone to 5 mg per day. He physician has reported that his polymyositis has gone into remission.

Example 27

A gum was prepared by mixing 100 g of presweetened gum base with 10 g of 1% high molecular weight (>1,000,000) sodium hyaluronate (Collaborative Laboratories, Inc.) and 2 mL of 100% Spearmint Oil. The gum was heated for approximately 10 seconds in a microwave until it was soft enough to knead in the glycosaminoglycan and essential oil. All components were kneaded together until a paste was produced. To the paste was added powdered sugar until the consistency was acceptable to cut into strips thus producing chewable gum. This gum, when chewed, dissolved within approximately 5 minutes and was used to treat the pain and inflammation of a sore throat, esophagitis, tonsilitis, gastritis, headache, and arthritis. In all cases, the individuals being treated reported that the gum was effective in treating their condition or disease.

A more chewable gum can be produced by adding excipients which produce thickening. Also complex carbohydrates alone (e.g. without essential oil(s)) can be used in the various formulations to treat the conditions as described above also in the delivery systems as mentioned above. The latter composition of one or more glycosaminoglycans can be used alone or combined with other mucosally or orally safe drugs or compounds to obtain similar results.

Example 28

A 54 year old female suffering from chronic osteoarthritis of both knees and spondylosis in the lower back, was attempting to control the pain in her knees and lower back by using Napralan (500 mg, BID), Pycnogenol (100 mg, BID), Glucosamine (750 mg, BID) and Chondroitin Sulfate (1000 mg, BID). Even on this regimen, there was a requirement for Depomedrol in the lower back approximately every 6 months. This individual presented suffering from sciatica associated with the spondylosis as well as severe pain and swelling in both knees, particularly in the left knee, which caused a noticeable limp (left knee). X-rays indicated that there was no cartilage remaining in either knee. She was asked what happened when she did not take the Glucosamine and Chondroitin Sulfate. She answered that she was almost unable to walk, certainly could not easily go down stairs. If the Pynogenol was also removed from the diet, the individual indicated that she could not tolerate the pain. She also reported that she had an active gastric ulcer that was controlled by taking 4 Pepcid AC per day. Initially, this patient was told to stop taking the Chondroitin Sulfate and Glucosamine and take 1.0 mL BID of liquid 1% sodium hyaluronate (10 mg) with an approximate molecular weight of 500,000 to 1,000,000. One day after starting this regime (without the Chondroitin Sulfate and Glucosamine) the patient reported feeling much better. She reported that she had no knee pain and her sciatica had disappeared. This patient continued the regimen and has been able to discontinue the use of the Pycnogenol as well. The patient reports a surprising improvement in her mobility. After taking the sodium hyaluronate for 2 years she is able to exercise by bicycling, walk without a limp and climb stairs easily. Unexpectedly, this patient has been able to discontinue taking the Pepcid AC and has had no exacerbation of her gastric ulcer and gastritis. Follow x-rays of her stomach have indicated a cure of her ulcer. It is believed that the mucosal glycosaminoglycan provided a soothing effect for the gastric ulcer as she reported an immediate improvement within one week of starting the mucosal hyaluronic acid. She was able to discontinue taking the Pepcid AC at that time.

Example 29

The patient from EXAMPLE 28 had had extensive surgery on her left hand approximately 20 years prior to joining this experiment. The surgery had involved removal of a significant portion of the tissue structure of the hand, an abdominal flap and skin grafts. She had developed adhesions on the tendons of the hand and did not have much use of this hand prior to taking the preparation of this invention. Indeed, at the start of this experiment, the hand was so swollen from adhesion irritation that the structure of the hand could not be delineated. Within 9 months of beginning the mucosal hyaluronic acid treatment she noted that she could easily make a fist, that the swelling in the hand was non-existent and that the structure of the hand, including blood vessels, could now be seen. There was no more pain from the irritation of the adhesions. Follow-up with her reconstructive surgeon indicated that the adhesions were resolved. The surgeon was totally surprised—he had not seen such extensive adhesions resolve. It is apparent that preparations of this invention, when taken orally or mucosally can treat and prevent adhesion formation post surgery.

Example 30

In order to determine whether low doses of other complex carbohydrates taken orally or mucosally could show effects similar to hyaluronic acid, 3 patients presenting with oeteoarthritis, rheumatoid arthritis and dental pain were treated with chondroitin sulfate. The two patients with osteo and rheumatoid arthritis had been using chondroitin sulfate (1000 mg BID) and glucosamine (500 mg BID) with some reported success. They were instructed to discontinue taking these products and substitute the compositions of the immediate invention. A 5% (wt/vol) solution of chondroitin sulfate (Infinity Laboratories, Inc) without essential oil was prepared. This was dispensed into 30 ml bottles and provided to the three patients with instructions to take 1.0 mL orally BID, holding it in the mouth for approximately 10 seconds prior to swallowing it. This represented a dose of 5 mg BID. This provided relief within 15 minutes. However, the relief lasted only 3-4 hours. The patients reported that they had to take the chondroitin Sulfate solution three times per day to treat their pain. After two months of this regimen, the two arthritis patients were given a mixture of the 5% chondroitin sulfate and 1% high molecular weight hyaluronic acid. They were instructed to take this as often as necessary. Each reported that this product was effective when taken only 2 times per day and the effect lasted from 8 to 10 hours. This demonstrates that a mixture of low and high molecular weight complex carbohydrates is more effective and that significantly lower doses (100 to 1000 fold less) of chondroitin sulfate are required for effective treatment of osteoarthritis and rheumatoid arthritis than are used in oral solid forms currently sold for these uses.

Example 31

A batch of lozenges containing hyaluronic acid was prepared as follows:
1. Prepare a sodium hyalurate solution containing 1% sodium hyaluronate obtained from Lifecore Biomedical (approx. 500,000 mw) by mixing 500 mL of the sodiumhyaluronate, 5.0 mL Oil of Wintergreen to produce a final concentration of 1% vol/vol, 2.5 mL Peppermint Oil to produce a final concentration of 0.5% vol/vol and 1.0 mL Spearmint Oil to produce a final concentration of 0.2% vol/vol.
2. Add 2 cups of cane sugar, ⅔ cup of corn syrup and ¾ cup water to a kettle. Bring the mixture to a boil by heating to 290-300° F. as measured using a candy thermometer (without stirring). A lid was kept on the kettle initially to wash down the sides of the kettle for the first few minutes.
3. Add 50 mL of the 1% hyaluronic acid mixture.
4. Add 6-8 drops of green liquid food coloring.
5. Spread the boiling liquid onto a cookie sheet and spray the top lightly with PAM. Cut immediately into small squares using a pizza cutter sprayed with PAM.
6. After the squares (lozenges) have cooled weigh groups of 10 pieces to determine consistency.

| Group 1 | 26.4 g | 2.64 g/lozenge |
| Group 2 | 29.7 g | 2.97 g/lozenge |
| Group 3 | 25.4 g | 2.54 g/lozenge |
| Group 4 | 26.1 g | 2.61 g/lozenge |
| Group 5 | 28.6 g | 2.86 g/lozenge |

Average weight per lozenge=2.7 g
Total weight of all lozenges=587.4 g
The amount of hyaluronic acid per lozenge=approx. 2.3 mg A 42 year old female raquetball professional suffering from chondromalacia of both knees and who had been using the topical preparation was given 10 lozenges to use for determination of the effect of the mucosally-administered hyaluronic acid on her chondromalacia. After sucking on the first two lozenges, she noted that her knees did not bother her while playing raquetball. She has reported that if she sucks a lozenge prior to playing raquetball, her knees do not bother her for several hours. Chondromalacia is a condition similar to osteoarthritis wherein there is degradation of the cartilage.

Example 32

A 55 year old female who suffers from a bulging cervical disc at C5-C6 agreed to try the hyaluronic lozenges (from Example 29) in place of Naproxen to suppress her constant headaches and neck pain. She was given 10 lozenges to use for determination of the effect of the hyaluronic acid lozenges. The patient was told to discontinue use of Naproxen and to report any effect, if any, after sucking each lozenge. After using all 10 lozenges, the patient reported the following:

| Day 1 | |
| --- | --- |
| After finishing 1 lozenge | No noticeable effect |
| After finishing 2 lozenges | Perhaps an effect, not sure |
| After finishing 3 lozenges | Headache gone (the 3 lozenges were used over a period of 8 hours) |
| Day 2 | |
| First thing in AM took 1 lozenge | Headache significantly reduced |
| Took a second lozenge | Headache gone within 30 minutes |
| Took a 3$^{rd}$ lozenge later in day | Headache did not return (the 3 lozenges were used over a period of 8 hours) |
| Day 3 | |
| Woke up with headache— 1 lozenge | Headache significantly reduced |
| Took a second lozenge | Headache gone within 15 minutes |
| Took a 3rd lozenge in PM | Headache did not return (the 3 lozenges were used over a period of 8 hours) |

Patient did not take Naproxen or any other anti-inflammatory drug during these three days. She reported that she normally could not have gone one day without taking Naproxen.

Example 33

The 42 year old female of EXAMPLE 29 developed a sore throat as a result of post nasal drip from a cold or sinus infection. She requested additional lozenges to determine their effect on her sore throat. After taking a single lozenge, she reported that her throat felt much better and her post nasal drip seemed to be significantly reduced. She was able to suppress her sore throat by taking 3 lozenges per day.

Example 34

A 54 year old female was suffering from post nasal drip associated with allergies. She began taking the hyaluronic acid lozenges as described in EXAMPLE 29 and reported that her post nasal drip was greatly reduced. She reported that she could take 3 lozenges per day and control the postnasal drip.

Example 35

A 48 year old female singer who was suffering from chronic bronchitis (3 months) to the point that she was unable to sing was given a solution containing a mixture of a low and high molecular weight hyaluronic acid (Prepared as in EXAMPLE 4). She was told to take 5 drops morning and evening, holding it in her mouth for about 10 seconds before swallowing. This represented a dose of 5 mg twice per day (10 mg/day total). She reported that within 3 days of starting the oral/mucosal hyaluronic acid her sinuses began to drain profusely. This lasted for 2 days after which her bronchitis disappeared. She continued taking the hyaluronic acid for a period of 14 days and reported that her bronchitis had cleared up and she was, once again, able to sing.

Example 36

A 46 year old female was taking mucosally-administered sodium hyaluronate prepared as in EXAMPLE 4 for treatment of bone spurs on her feet (ball and heal of both feet). She worked in retail sales and was on her feet on concrete floors for 8 hours each day. She reported that taking 10 mg twice per day allowed her to work comfortably each day.

Prior to taking the hyaluronic acid preparation of this invention, this patient had visited a hand surgeon to have a ganglion at the base of the middle finger on her left hand removed. It was the size of a pea and had been getting larger for the past 3 years. She had not been able to schedule surgery due to her work requirements. After taking the hyaluronic acid of this invention for a period of 3 months, she noticed that the ganglion was disappearing. By 5 months post initiation of mucosal hyaluronic acid, the ganglion was completely resolved. It appears that inflamed nerve bundles (ganglion) can be treated and prevented with the compositions of this invention.

All cited patents, provisional applications and publications referred to in this application are herein incorporated by reference.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A composition which comprises: a pharmacologically effective amount of at least one orally ingestable or mucosally absorbable low purity hyaluronic acid or salt thereof, comprising at least one fraction having a molecular weight in the range of greater than 1,000,000 daltons, as measured using a protein standard/intrinsic viscosity, with the proviso that said composition does not contain an essential oil as an active ingredient, and wherein the low purity hyaluronic acid or salt thereof contains up to 5% by weight protein contaminants, wherein said low purity hyaluronic acid or salt thereof is defined as causing reactions when injected into owl monkey eyes but will not cause reactions when applied to the skin of mammals or when delivered orally or mucosally to mammals, and
   an oral or mucosal carrier selected from the group consisting of a liquid, an emulsion, a suspension, a cream, an ointment, a gel, a foam, a solid, a powder, water, a solution, a spray, a throat spray, a drink, a drink mix, a food, a candy, a mouthwash, a toothpaste, a gargle, a vaporizer liquid, a gum, a lozenge, an ingestable gel, an ingestable foam, an ingestable capsule, a tablet, an ingestable tablet, an ingestable dissolvable tablet, a suppository, and an ingestable nutritional supplement.

2. A method of treatment of inflammation, pain or itching which comprises orally or mucosally administering to a mammal the composition of claim 1, wherein the inflammation, pain or itching does not include Attention Deficit Hyperactivity Disorder (ADHD).

3. The method of claim 2, wherein said application is made orally.

4. The method of claim 2, wherein said oral or mucosal carrier is selected from the group consisting of a liquid, an emulsion, a suspension, a cream, an ointment, a gel, a foam, a solid, a powder and a gum.

5. The method of claim 2, wherein said inflammation, pain or itching results from arthritis, bursitis, athletic injuries, tendonitis, trauma, gastritis, colitis, esophagitis, bronchitis, sore throat, tonsilitis, tendonitis, fibromyalgia, TMJ, dental pain, bruising, poor circulation, muscle cramps, tired feet, allergies, poison ivy, insect bites/stings, asthma, anaphylaxis, surgery, childbirth, sunburn, burns, edema related to diabetes, decubitus ulcers, superficial cuts and scrapes, open wounds, dry skin, psoriasis, adhesion formation post surgery, scar formation post surgery, wound healing, ganglion formation, and wrinkles.

6. A method for treating inflammation, pain or allergy-related diseases and conditions which comprises orally or mucosally administering to a mammal a therapeutically effective amount of the composition of claim 1, wherein the inflammation, pain or allergy-related diseases and conditions does not include Attention Deficit Hyperactivity Disorder (ADHD).

7. A method for treating inflammation, pain or allergy-related diseases and conditions which comprises orally administering to a mammal a therapeutically effective amount of the composition of claim 1, wherein the inflammation, pain or allergy-related diseases and conditions does not include Attention Deficit Hyperactivity Disorder (ADHD).

8. A method for treating inflammation, pain or allergy-related diseases and conditions which comprises mucosally administering to a mammal a therapeutically effective amount of the composition of claim 1, wherein the inflammation, pain or allergy-related diseases and conditions does not include Attention Deficit Hyperactivity Disorder (ADHD).

9. The method of claim 7 or 8 wherein the inflammation, pain, or allergy-related diseases and conditions are selected from the group consisting of arthritis, bursitis, athletic injuries, tendonitis, trauma, anaphylaxis, surgery, childbirth, gastritis, colitis, esophagitis, bronchitis, sore throat, tonsilitis, tendonitis, fibromyalgia, TMJ, dental pain, bruising, poor circulation, muscle cramps, tired feet, allergies, poison ivy, insect bites/stings, asthma, sunburn, burns, edema related to diabetes, decubitus ulcers, superficial cuts and scrapes, open wounds, dry skin, psoriasis, adhesion formation post surgery, scar formation post surgery, wound healing, ganglion formation, and wrinkles.

10. The composition according to claim 1, wherein said at least one hyaluronic acid or salt thereof further comprises a fraction having a molecular weight in the range of from 1,000 to less than 50,000 daltons.

11. The composition according to claim 1, wherein said at least one hyaluronic acid or salt thereof further comprises a fraction having a molecular weight in the range of from 100,000 to 300,000 daltons.

12. The composition according to claim 1, wherein the carrier is selected from the group consisting of a liquid, an emulsion, a suspension, a solution, a cream, a gel, a foam, a solid, a powder, a spray, a gum and an ointment.

13. The composition according to claim 1, wherein the carrier is selected from the group consisting of a liquid, a gel, a solution, a suspension, an emulsion, an ointment, a cream, a solid, a powder, a gum and a spray.

14. The method of claim 2, wherein said composition is administered to treat pain.

15. The method of claim 2, wherein said composition is an orally delivered pain-relieving composition.

16. The composition of claim 2, wherein said composition is a mucosally delivered pain-relieving composition.

17. The composition of claim 1, wherein the composition contains a maximum of 98% by weight hyaluronic acid.

18. A method for treating inflammation, pain or allergy-related diseases and conditions which comprises mucosally applying to a mammal a therapeutically effective amount of the composition of claim 1, wherein the inflammation, pain or allergy-related diseases and conditions does not include Attention Deficit Hyperactivity Disorder (ADHD).

19. The composition of claim 1, wherein said at least one low purity hyaluronic acid or salt thereof is of cosmetic or food grade and further comprises a fraction having a molecular weight in the range of from 1,000 to less than 50,000 or from 100,000 to 500,000.

20. The compositions according to claim 1, wherein the vaporizer liquid is a throat spray, the gum is a chewing gum or a dissolvable gum, the lozenge is throat lozenges, and the food is treats or candy.

21. An orally ingestible or mucosally absorbable pharmaceutical composition selected from the group consisting of a drink, a drink mix, food, candy, mouthwash, toothpaste, gargle, vaporizer, gum, lozenge, ingestable gel, ingestable foam, ingestable capsule, tablet, ingestable tablet, ingestable dissolvable tablet, suppository, and ingestable nutritional supplement, which comprises a pharmacologically effective amount of at least one low purity hyaluronic acid or salt thereof wherein said at least one low purity hyaluronic acid or salt thereof comprises at least one fraction having a molecular weight range greater than 1,000,000 daltons as measured using a protein standard/intrinsic viscosity, said composition does not contain an essential oil as an active ingredient, and wherein said low purity hyaluronic acid or salt thereof is defined as causing reactions when injected into owl monkey eyes but will not cause reactions when applied to the skin of mammals or when delivered orally or mucosally to mammals.

22. The composition of claim 21, wherein said low purity hyaluronic acid or salt thereof contains up to about 5% impurities selected from the group consisting of proteins, nucleic acids, teichoic acids, endotoxins and lipids.

23. An orally ingested or mucosally-absorbed pharmaceutical composition selected from the group consisting of drink, drink mix, food, candy, mouthwash, toothpaste, gargle, vaporizer, gum, lozenge, ingestable gel, ingestable foam, ingestable capsule, tablet, ingestable tablet, ingestable dissolvable tablet, suppository, and ingestable nutritional supplement, which comprises:
  an effective amount of at least one low purity hyaluronic acid or salt thereof for treating inflammation, wherein said at least one low purity hyaluronic acid or salt thereof comprises at least one fraction having a molecular weight range greater than 1,000,000 daltons as measured using a protein standard/intrinsic viscosity, wherein said low purity hyaluronic acid or salt thereof is defined as causing an inflammatory response when injected into owl monkey eyes but will not cause an adverse reaction when applied to the skin of mammals or when delivered orally or mucosally to mammals, and wherein the low purity hyaluronic acid or salt thereof contains up to 5% by weight protein contaminants, with the proviso that said composition does not contain an essential oil as the active ingredient.

24. Drink comprising the composition of claim 23.

25. Drink mix comprising the composition of claim 23.

26. Food comprising the composition of claim 23.

27. Candy comprising the composition of claim 23.

28. Mouthwash comprising the composition of claim 23.

29. Toothpaste comprising the composition of claim 23.

30. Gargle comprising the composition of claim 23.

31. Vaporizer comprising the composition of claim 23.

32. Gum comprising the composition of claim 23.

33. Lozenge comprising the composition of claim 23.

34. Ingestable gel comprising the composition of claim 23.

35. Ingestable foam comprising the composition of claim 23.

36. Ingestable capsule comprising the composition of claim 23.

37. Tablet comprising the composition of claim 23.

38. Ingestable tablet comprising the composition of claim 23.

39. Ingestable dissolvable tablet comprising the composition of claim 23.

40. Suppository comprising the composition of claim 23.

41. Ingestable nutritional supplement comprising the composition of claim 23.

42. The composition of claim 1, wherein the hyaluronic acid or salt thereof is in a total concentration of between 0.5% and 3.0% wt/vol.

43. A method for relieving joint pain or other discomforts associated with osteoarthritis, rheumatoid arthritis or joint disorders in a mammal comprising the step of delivering to said mammal by oral ingestion the composition of claim 1, wherein the carrier comprises a nutritional supplement administered in repeat low doses of between 0.0001 mg and 100 mg.

44. The method of claim 43, wherein the carrier further comprises food or water.

45. The method of claim 43, wherein the nutritional supplement is provided in capsule form.

46. The method of claim 43, wherein the mammal is a human, an equine, a canine, or feline species.

47. A method for reducing discomfort of fibromyalgia in a person afflicted with fibromyalgia comprising the step of delivering to said person by oral ingestion the composition of claim 1, wherein the carrier comprises a nutritional supplement in repeated low doses of between 0.0001 mg and 100 mg.

48. The method of claim 47,
  wherein the carrier further comprises food or water.

49. The method of claim 47, wherein the nutritional supplement is provided in capsule form.

50. A method for relieving joint pain or other discomforts associated with joint disorders in a mammal comprising the step of delivering to said mammal by oral ingestion the composition of claim 1, wherein the carrier comprises a nutritional supplement, a food or drink, wherein the effective amount of low purity hyaluronic acid, or a salt thereof in the composition, is administered in repeated low doses of between 0.0001 mg 100 mg.

51. The method of claim 47, wherein the nutritional supplement is provided in tablet form.

52. The method of claim 50, wherein the carrier further comprises food or water.

53. The method of claim 50, wherein the composition is provided in capsule form.

54. The method of claim 50, wherein the mammal is a human, an equine, a canine, or a feline species.

55. The method of claim 50, wherein the joint pain is the result of an arthritic condition.

56. The method of claim 55, wherein the arthritic condition is selected from the group consisting of osteoarthritis and rheumatoid arthritis.

57. The method of claim 50, wherein the joint pain is the result of an inflammatory condition.

58. A nutritional supplement comprising an nutritionally effective amount of at least one orally ingestable or mucosally absorbable low purity hyaluronic acid or salt thereof, comprising at least one fraction having a molecular weight in the range of greater than 1,000,000 daltons, as measured using a protein standard/intrinsic viscosity, with the proviso that said composition does not contain an essential oil as an active ingredient, and wherein the low purity hyaluronic acid or salt thereof contains up to 5% by weight protein contaminants, and a food or drink carrier, the nutritional supplement provided in an orally ingestible dosage form, wherein the hyaluronic acid or a salt thereof is present in an amount of between 0.01% and 5.0 wt/vol., wherein said low purity hyaluronic acid is defined as causing reactions when injected into owl monkey eyes but will not cause reactions when applied to the skin of mammals or when delivered orally or mucosally to mammals.

59. The nutritional supplement of claim 58, wherein the effective amount of hyaluronic acid is present in a dose of between 0.0001 mg and 100 mg.

60. The nutritional supplement of claim 58, wherein the orally ingestible dosage form is a capsule or gel cap.

61. Food or treat for horse or dog comprising the composition of claim 1, wherein the active ingredient is present in a dose between 0.001 mg and 100 mg.

62. The method of claim 2, wherein said are administered in multiple low doses of between 0.0001 mg and 100 mg.

63. The composition of claim 1, wherein the adverse reaction is selected from the group consisting of irritation, blistering and rash, and combinations thereof.

64. The composition of claim 1, wherein the hyaluronic acid or salt thereof is present in a total concentration of between 0.01% and 3.0% wt/vol of the composition.

65. The composition of claim 1 wherein the low purity hyaluronic acid or salt thereof is present in an amount of between 0.01% and 5.0% wt/vol.

* * * * *